United States Patent
Scibola et al.

(10) Patent No.: US 9,556,386 B2
(45) Date of Patent: Jan. 31, 2017

(54) SEPARATION OF HYDROCARBON FAMILIES OR OF INDIVIDUAL COMPONENTS BY CONSECUTIVE EXTRACTIVE DISTILLATIONS PERFORMED IN A SINGLE COLUMN

(71) Applicant: SIME S.R.L., Rosignano Marittimo (IT)

(72) Inventors: Luciano Scibola, Crema (IT); Stefano Favilli, Rosignano Marittimo (IT)

(73) Assignee: SIME S.R.L., Rosignano Marittimo (IT)

( * ) Notice: Subject to any disclaimer, the term of this patent is extended or adjusted under 35 U.S.C. 154(b) by 317 days.

(21) Appl. No.: 14/365,739

(22) PCT Filed: Dec. 14, 2012

(86) PCT No.: PCT/EP2012/075519
§ 371 (c)(1),
(2) Date: Jun. 16, 2014

(87) PCT Pub. No.: WO2013/087831
PCT Pub. Date: Jun. 20, 2013

(65) Prior Publication Data
US 2014/0353216 A1 Dec. 4, 2014

(30) Foreign Application Priority Data

Dec. 15, 2011 (IT) ............................. MI2011A2271

(51) Int. Cl.
*C10G 7/08* (2006.01)
*B01D 3/14* (2006.01)
(Continued)

(52) U.S. Cl.
CPC ............... *C10G 7/08* (2013.01); *B01D 3/141* (2013.01); *B01D 3/40* (2013.01); *C07C 7/08* (2013.01);
(Continued)

(58) Field of Classification Search
CPC ............. C10G 7/08; C10G 2400/30; C10G 2300/1096; C10G 2300/203; C10G 2400/02; C10G 2300/4056; C07C 7/08; B01D 3/40; B01D 3/141
See application file for complete search history.

(56) References Cited

U.S. PATENT DOCUMENTS 2,771,494 A 11/1956 Weedman
2,846,485 A 8/1958 Meason et al.
(Continued)

FOREIGN PATENT DOCUMENTS

DE 10019196 C1 9/2001
DE 10018434 A1 10/2001
(Continued)

OTHER PUBLICATIONS

International Search Report dated Feb. 15, 2013 issued in PCT/EP2012/075519.

*Primary Examiner* — Randy Boyer
*Assistant Examiner* — Juan Valencia
(74) *Attorney, Agent, or Firm* — Scully, Scott, Murphy & Presser, P.C.

(57) ABSTRACT

A column for consecutive extractive distillations, in particular of crude hydrocarbon mixes comprising aromatic, naphthene and paraffin hydrocarbons. The invention also relates to methods for separating and recovering the components of a crude hydrocarbon mix comprising aromatic, naphthene and paraffin hydrocarbons by consecutive extractive distil-
(Continued)

lations provided by means of the column for consecutive extractive distillations, to which the invention also relates.

23 Claims, 18 Drawing Sheets

(51) Int. Cl.
*B01D 3/40* (2006.01)
*C07C 7/08* (2006.01)

(52) U.S. Cl.
CPC . *C10G 2300/1096* (2013.01); *C10G 2300/203* (2013.01); *C10G 2300/4056* (2013.01); *C10G 2400/02* (2013.01); *C10G 2400/30* (2013.01)

(56) References Cited

U.S. PATENT DOCUMENTS

| | | | |
|---|---|---|---|
| 2,849,396 A | 8/1958 | Nelson | |
| 3,034,969 A | 5/1962 | Makin, Jr. | |
| 3,591,490 A | 7/1971 | Muller et al. | |
| 3,723,526 A | 3/1973 | Edgerton | |
| 4,278,505 A | 7/1981 | Danulat et al. | |
| 4,503,369 A | 3/1985 | Nishijima et al. | |
| 4,664,783 A | 5/1987 | Preusser et al. | |
| 4,921,581 A | 5/1990 | Lee et al. | |
| 4,944,849 A | 7/1990 | Lee | |
| 4,948,470 A | 8/1990 | Lee | |
| 4,948,472 A | 8/1990 | Lee et al. | |
| 4,954,224 A | 9/1990 | Brown et al. | |
| 4,955,468 A | 9/1990 | Lee | |
| 5,022,981 A | 6/1991 | Forte | |
| 5,032,232 A | 7/1991 | Lee et al. | |
| 5,055,162 A | 10/1991 | Brown et al. | |
| 5,069,757 A | 12/1991 | Brown | |
| 5,139,651 A | 8/1992 | Forte | |
| 5,310,480 A | 5/1994 | Vidueira | |
| 5,399,244 A | 3/1995 | Gentry et al. | |
| 5,401,365 A | 3/1995 | Chen et al. | |
| 5,563,315 A | 10/1996 | Forte | |
| 6,005,157 A | 12/1999 | Lee et al. | |
| 6,514,387 B1 | 2/2003 | Emmrich et al. | |
| 6,616,831 B1 | 9/2003 | Gentry et al. | |
| 6,660,899 B2 | 12/2003 | McKim et al. | |
| 6,781,026 B2 | 8/2004 | Lee | |
| 7,078,580 B2 | 7/2006 | Tian et al. | |
| 7,666,299 B2 | 2/2010 | Wu et al. | |
| 2001/0049462 A1 | 12/2001 | Lee | |
| 2005/0199482 A1 | 9/2005 | Heida | |
| 2008/0161618 A1 | 7/2008 | Zimmermann et al. | |
| 2008/0228019 A1 | 9/2008 | Heida | |
| 2009/0105514 A1 | 4/2009 | Lee et al. | |
| 2009/0255853 A1 | 10/2009 | Lee et al. | |
| 2010/0270213 A1 | 10/2010 | Noe | |

FOREIGN PATENT DOCUMENTS

| | | |
|---|---|---|
| DE | 10135585 C1 | 9/2002 |
| EP | 1112769 A1 | 7/2001 |
| EP | 2266674 A1 | 12/2010 |

SEPARATION OF HYDROCARBON FAMILIES OR OF INDIVIDUAL COMPONENTS BY CONSECUTIVE EXTRACTIVE DISTILLATIONS PERFORMED IN A SINGLE COLUMN

The present invention relates to a method and an apparatus for mutually separating families of polar hydrocarbons from non-polar hydrocarbons, such as aromatics from non-aromatics and naphthenes from n-paraffins and i-paraffins.

It ranges from the separation of mixes of hydrocarbons of the various families cited above to the separation of individual components of the individual families, such as for example benzene from C6 non-aromatics, cyclohexane and/or methylcyclopentane from C6 n+iso-paraffins, n-hexane from C6 cycloalkanes with extension also to the C5 fraction for cyclopentane.

The present invention relates to the separation, by consecutive extractive distillations performed in a single column, of mixes of aromatics and mixes of non-aromatics and subsequently of mixes of naphthenes from mixes of n+iso-paraffins.

Particularly, the mixes of interest can comprise BT aromatics (benzene, toluene), BTX aromatics (benzene, toluene, xylenes), TX aromatics (toluene, xylenes), TXC9 aromatics (toluene, xylenes and C9 aromatics), XC9 aromatics (xylenes and C9 aromatics) and the corresponding mixes of non-aromatics (C6C7, C6C7C8, C7C8, C7C8C9, C8C9) and mixes of naphthenes (N6N7, N6N7N8, N7N8, N7N8N9, N8N9) from the corresponding mixes of paraffins (P6P7, P6P7P8, P7P8, P7P8P9, P8P9).

More particularly, the components of interest are benzene (aromatics family), cyclohexane and/or methylcyclopentane and/or cyclopentane (naphthene family) and n-hexane/C6 paraffins (paraffin family).

The invention also relates to the integrated use of solvents for consecutive separations of aromatics from non-aromatics and of naphthenes from (n+iso)paraffins, with the associated process and management simplifications.

Separations between polar hydrocarbons and non-polar hydrocarbons are performed industrially by using liquid-liquid extractions and/or extractive distillations or sometimes azeotropic distillations.

The difficulty of separation of components or hydrocarbon families that have relative volatilities close to 1 and very close boiling points is overcome by using solvents or mixes of solvents, which:
  either have higher affinity for some components or hydrocarbon families, influencing their volatility with respect to the others;
  or form azeotropes with some component, said azeotropes having volatilities that are clearly different from the others that constitute the mixes to be treated.

The use of extractive distillation to separate aromatics, in particular to separate benzene, toluene and xylenes from non-aromatics, where the non-aromatics have close boiling points, is reported in several patents (U.S. Pat. Nos. 3,591,490, 3,723,526, 4,503,369, 4,664,783, 5,022,981, 5,032,232, 5,069,757, 5,139,651, 5,310,480, 5,399,244, 5,401,365, 5,563,315, 6,616,831, 6,660,899, 6,781,026, 7,078,580, 7,666,299, U.S. Patent Application Publication Nos. 2001/0049462, 2009/0105514, 2009/0255853, 2010/0270213.

U.S. Pat. Nos. 2,771,494, 2,846,485, 2,849,396, 3,034,969, 4,921,581, 4,944,849, 4,948,470, 4,948,472, 4,954,224, 4,955,468, 5,055,162, 6,005,157 describe methods for separating cycloalkanes in the C5-C10 range from other hydrocarbons and in particular from normal and iso paraffins. Alternative solvents and solvent mixes suitable for the purpose are presented. These U.S. patents are incorporated herein by reference.

U.S. Pat. No. 4,278,505 shows a process for the recovery of n-hexane with N-methyl pyrrolidone: this US patent also is incorporated herein by reference.

The separation of hydrocarbon families such as aromatics (C6-C9+), present in reformates, pyrolysis gasolines, naphthas or condensates/NGL of various origin, from naphthenes (C6-C9+) and paraffins (C6-C9+), i.e., of the same hydrocarbon families from narrower cuts (for example C6 cut) of the same origin (reformate or pyrolysis gasoline or naphthas or condensates/NGL) currently is provided by means of a series of process steps such as:
  a) desulfuration of the charges, with removal/saturation of the olefins/diolefins;
  b) optional pre-fractioning of the wide cuts into narrow cuts;
  c) separation by extraction/extractive distillation of the aromatics from the non-aromatics;
  d) separation of naphthenes from paraffins for the production of cyclohexane and/or methylcyclopentane and/or paraffin solvents such as n-hexane, n-heptane is obtained optionally by further extraction/extractive distillation and optional fractionation/additional treatment (hydrogenation of residual benzene) for the isolation of the hydrocarbon of interest.

Industrial practice currently very often provides for high-octane reformate to be "split" into a C6-C7 cut and a C8+ cut from which the aromatics of interest are subsequently recovered (benzene and toluene from C6-C7 cut by extraction/extractive distillation and subsequent fractionation and mixed xylenes of interest from the C8+ cut by fractionation, isomerization, separation by absorption on molecular sieves and/or crystallization, etc.). Preventive splitting of the reformate is dictated by the practical absence of non-aromatics in the C8+ cut of the reformate (FIGS. 1, 2, 5).

Pyrolysis gasoline also is fractionated in narrow cuts before proceeding with the separation of the aromatics of interest from the non-aromatics.

In this case also, industrial practice provides for the separation of a C6-C7 cut and a C8+ cut. In this second case, the C8+ are very often intended for gasoline pools.

Moreover, it is of industrial interest to produce cyclohexane from naphthas and/or condensates, NGL.

Currently, almost all cyclohexane is produced by hydrogenation of benzene because the separation of cyclohexane from the other hydrocarbons that accompany it in naphthas/NGL is currently complicated and expensive.

The production of n-hexane is intended for use as a solvent for polymerization in solution (PE and other polymers), as a component of glues and paints, and as a solvent in the extraction of vegetable oils. The type of use determines the n-hexane titer and the admissible impurities in the product (in particular the benzene content).

Merely by way of example, Tables 1, 2, 3, 4 illustrate the concentrations of naphthenes and paraffins (potential non-aromatics with any olefins) that can be found in some feedstock/products of refineries/petrochemical plants.

The olefins that are present in reformates (in particular in reformates from CCR) have affinities for solvents comparable to those of naphthenes and therefore are removed upstream of the treatment for recovery of paraffins/naphthenes.

The "natural" destination of non-aromatic refinates from extraction/extractive distillation is respectively that of raw material for steam-cracking, paraffin refinate from reformate or C6 cut from reformate and reforming charge, naphthene refinate from pyrolysis gasoline or from C6-C7 cut from pyrolysis gasoline.

From desulfurated naphthas and NGL it is observed that the removal of benzene and of benzene precursors (particularly cyclohexane) from them would make it possible to then obtain from reforming gasolines that are already standards-compliant in terms of benzene content for the automotive market.

The above cited uses of non-aromatics, with upgrades that are certainly not high, in any case entail technical and economic problems, such as:
- the presence of large quantities of MCP (methylcyclopentane) in the naphthene refinate, which can be converted to aromatics in reforming with poor yields and with substantial degradation to coke;
- handling and storage costs if the S/cracking or reforming do not take place at the same site as the reforming or S/cracking respectively: these costs can cancel the advantages of a correct allocation of the raw material;
- the presence of traces of the extraction solvent, which can be the source of fouling in S/cracking ovens (paraffin refinate) as well as in reforming reactors (naphthene refinate);
- the high percentage of iso-paraffins with respect to n-paraffins in paraffin refinates, which facilitates the conversion to propylene instead of ethylene in S/cracking with high underproduction of methane.

In summary, the upgrading of said byproducts seldom exceeds that of a normal S/cracking charge, i.e., of a normal commercial naphtha.

In order to upgrade these byproducts, today important investments, for example additional extractive distillation units, would be necessary in order to:

a) remove the naphthenes from the paraffin refinate, obtaining paraffin solvents with an n-paraffin titer of more than 99% or, by fractionation, n-hexane/n-heptane usable as solvents, recycling to local reforming the separated naphthenes without increases in logistics costs and the (octane enriched) iso-paraffin stream to gasoline blending;

b) separate the naphthenes from the naphthene refinate, obtaining a paraffin byproduct that can be recycled conveniently to the local S/cracking and optionally separating the methylcyclopentane from the cyclohexane with upgrading of both (commercial sale of solvents or optional isomerization to cyclohexane for the MCP; use as a solvent or charge for adipic acid for the cyclohexane).

Considering the volumes of the extraction byproducts that are available, it is highly desirable to find methods for simplifying the processes for the separation of said products.

It should be noted that the arguments given above also apply to the case of petrochemical sites in which both reforming and S/cracking units are present or where petrochemical sites interested in the upgrading of pure aromatic, naphthene, paraffin components are adjacent to refineries interested in removing benzene or naphthene precursors thereof and/or n-paraffins from gasoline pools.

If the cuts of the two origins (reformate/pyrolysis gasoline) are mixed, the corresponding refinate has a composition that is intermediate between the one of the pure paraffin refinate and the one of pure naphthene refinate.

Consequently, extractive distillation of the refinate provides naphthenes and paraffins that can be conveniently recycled respectively to the reforming and S/cracking units, i.e., it allows the optional separation of individual n-paraffins or individual naphthenes with possible additional investments (distillations).

TABLE 1

| PRODUCT COMPONENTS | UNITS | Reformed C6+ | Potential Non-Aromatics (P + N) |
|---|---|---|---|
| i-PENTANES | % Vol. | 0.31 | 1.04 |
| n-PENTANE | % Vol. | 0.87 | 3.13 |
| i-HEXANES | % Vol. | 9.51 | 32.99 |
| n-HEXANE | % Vol. | 3.91 | 13.54 |
| i-HEPTANES | % Vol. | 7.51 | 26.04 |
| n-HEPTANE | % Vol. | 2.03 | 6.94 |
| i-OCTANES | % Vol. | 2.03 | 6.94 |
| n-OCTANE | % Vol. | 0.56 | 2.08 |
| i-NONANES | % Vol. | 0.47 | 1.74 |
| n-NONANE | % Vol. | 0.10 | 0.35 |
| TOTAL PARAFFINS | % Vol. | 27.30 | 94.79 |
| OLEFINS | % Vol. | 0.89 | |
| TOTAL OLEFINS | % Vol. | 0.89 | |
| CYCLOPENTANE | % Vol. | 0.21 | 0.73 |
| METHYLCYCLOPENTANE | % Vol. | 0.31 | 1.08 |
| CYCLOHEXANE | % Vol. | 0.01 | 0.03 |
| C7 NAPHTHENES | % Vol. | 0.44 | 1.53 |
| C8 NAPHTHENES | % Vol. | 0.50 | 1.74 |
| C9 NAPHTHENES | % Vol. | 0.03 | 0.10 |
| TOTAL NAPHTHENES | % Vol. | 1.50 | 5.21 |
| BENZENE | % Vol. | 4.67 | |
| TOLUENE | % Vol. | 16.18 | |
| C8 AROMATICS | % Vol. | 23.02 | |
| C9+ AROMATICS | % Vol. | 26.44 | |
| TOTAL AROMATICS | % Vol. | 70.31 | |

TABLE 2

| PRODUCT COMPONENTS | UNITS | Reformed C6 Cut | Potential Non-Aromatics (P + N) C6 Cut |
|---|---|---|---|
| i-BUTANE | % Weight | 0.03 | 0.05 |
| n-BUTANE | % Weight | 0.09 | 0.15 |
| i-PENTANES | % Weight | 0.99 | 1.68 |
| n-PENTANE | % Weight | 0.97 | 1.65 |
| i-HEXANES | % Weight | 16.92 | 28.77 |
| n-HEXANE | % Weight | 11.76 | 19.99 |
| i-HEPTANES | % Weight | 19.99 | 33.99 |
| n-HEPTANE | % Weight | 3.17 | 5.39 |
| i-OCTANES | % Weight | 0.67 | 1.14 |
| n-OCTANE | % Weight | 0.02 | 0.03 |
| TOTAL PARAFFINS | % Weight | 54.61 | 92.84 |
| OLEFINS | % Weight | 2.70 | |
| TOTAL OLEFINS | % Weight | 2.70 | |
| CYCLOPENTANE | % Weight | 0.32 | 0.54 |
| METHYLCYCLOPENTANE | % Weight | 1.84 | 3.13 |
| CYCLOHEXANE | % Weight | 0.25 | O.43 |
| C7 NAPHTHENES | % Weight | 1.67 | 2.84 |
| C8 NAPHTHENES | % Weight | 0.13 | 0.22 |
| C9 NAPHTHENES | % Weight | 0.00 | 0.00 |
| TOTAL NAPHTHENES | % Weight | 4.21 | 7.16 |
| BENZENE | % Weight | 26.35 | |
| TOLUENE | % Weight | 12.01 | |
| C8 AROMATICS | % Weight | 0.12 | |
| C9+ AROMATICS | % Weight | 0.00 | |
| TOTAL AROMATICS | % Weight | 38.48 | |

TABLE 3

| PRODUCT COMPONENTS | UNITS | Hydrogenated Pyrolysis Gasoline C6-C7 Cut | Potential Non-Aromatics (P + N) C6-C7 Cut |
|---|---|---|---|
| i-PENTANES | % Weight | 0.01 | 0.07 |
| n-PENTANE | % Weight | 0.02 | 0.13 |
| 2+3Methylpentane and other i-Hexanes | % Weight | 2.32 | 15.47 |
| n-HEXANE | % Weight | 2.37 | 15.80 |
| 2+3Methylhexane and other i-HEPTANES | % Weight | 0.80 | 5.34 |
| n-HEPTANE | % Weight | 0.38 | 2.53 |
| 2+3Methyl-heptane/isoctanes | % Weight | 0.31 | 2.07 |
| n-OCTANE | % Weight | 0.04 | 0.27 |
| TOTAL PARAFFINS | % Weight | 6.25 | 41.67 |
| OLEFINS | % Weight | 0.01 | |
| TOTAL OLEFINS | % Weight | 0.01 | |
| CYCLOPENTANE | % Weight | 0.045 | 0.30 |
| METHYLCYCLOPENTANE | % Weight | 5.755 | 38.37 |
| CYCLOHEXANE | % Weight | 1.65 | 11.00 |
| Dimethylcyclopentane $C_7N$ and Methylcyclohexane $C_7N$ | % Weight | 1.30 | 8.66 |
| TOTAL NAPHTHENES | % Weight | 8.75 | 58.33 |
| BENZENE | % Weight | 67.14 | |
| TOLUENE | % Weight | 17.85 | |
| C8 AROMATICS | % Weight | 0.00 | |
| TOTAL AROMATICS | % Weight | 84.99 | |

TABLE 4

| PRODUCT COMPONENTS | UNITS | Full-range desulfurated naphtha | Potential Non-Aromatics (P+N) |
|---|---|---|---|
| i-PENTANES | % Vol. | 0.13 | 0.15 |
| n-PENTANE | % Vol. | 0.52 | 0.61 |
| i-HEXANES/N-HEXANE | % Vol. | 7.84 | 9.16 |
| i-HEPTANES/N-HEPTANE | % Vol. | 12.58 | 14.70 |
| i-OCTANES/N-OCTANE | % Vol. | 15.52 | 18.14 |
| i-NONANES/N-NONANE, i-DECANES/N-DECANES, i-UNDECANES/N-UNDECANES | % Vol. | 19.86 | 23.21 |
| TOTAL PARAFFINS | % Vol. | 56.45 | 65.97 |
| OLEFINS | % Vol. | 0.8 | |
| TOTAL OLEFINS | % Vol. | 0.8 | |
| CYCLOPENTANE | % Vol. | 0.19 | 0.22 |
| METHYLCYCLOPENTANE | % Vol. | 2.21 | 2.58 |
| CYCLOHEXANE | % Vol. | 2.26 | 2.64 |
| C7 NAPHTHENES | % Vol. | 9.34 | 10.92 |
| C8 NAPHTHENES | % Vol. | 5.06 | 5.91 |
| C9 NAPHTHENES | % Vol. | 10.06 | 11.76 |
| TOTAL NAPHTHENES | % Vol. | 29.12 | 34.03 |
| BENZENE | % Vol. | 1.23 | |
| TOLUENE | % Vol. | 3.32 | |
| C8 AROMATICS | % Vol. | 5.22 | |
| C9+ AROMATICS | % Vol. | 3.86 | |
| TOTAL AROMATICS | % Vol. | 13.63 | |

Therefore, the aim of the present invention is to provide an apparatus and a method for separating and recovering families of aromatics, naphthenes and paraffins and/or individual aromatic hydrocarbons from naphthene and paraffin hydrocarbons with reduction of investment costs and of the need for spaces to perform said processes.

An object of the present invention is to provide an apparatus and a method that allow reducing the extra investment costs required to provide the above mentioned improved upgrading of said paraffin/naphthene refinates and/or of said desulfurated naphthas or NGL, improving the profitability of the overall process.

A particular object of the invention is to provide such a method that allows reducing the overall energy demand with respect to known types of method.

Another particular object of the invention is to provide such a process that allows the integrated use of the solvents for consecutive separations of aromatics from non-aromatics and of naphthenes from paraffins (n+iso), achieving process and management simplifications.

This aim and these and other objects are achieved, according to the present invention, by means of consecutive extractive distillations, performed in an apparatus which is a fully partitioned column optionally provided with an internal channel for connection between the parts, so as to provide the separations of the above cited families of hydrocarbons and/or of individual hydrocarbons of said families in a consecutive way, substantially in a single extractive distillation apparatus.

A first aspect of the present invention provides a column for consecutive extractive distillations, particularly of a crude hydrocarbon mix constituted essentially by aromatic, naphthene and paraffin hydrocarbons, comprising a vertical elongated container provided with a head or top, a bottom and an internal partition wall that runs vertically from the bottom to the head of said container and divides its internal volume, forming a first longitudinal chamber and a second longitudinal chamber which are adjacent, inside said column, wherein each one of said chambers comprises at least four sections, of which a middle section, a solvent regeneration section arranged below said middle section, a section for separating an affine component which is arranged above said middle section and a section for the recovery of solvent entrained by a less affine fraction, said middle section being divided into a main section for stripping components that are not affine with the solvent, which is arranged conveniently but not necessarily toward the inside of the column, and a lateral rectification subsection for removing solvent from the affine components, arranged conveniently but not necessarily toward the outside of the column, by means of a vertical partition wall of the middle section arranged within the middle section, wherein said main section is open at the top and at the bottom and said subsection is open at the bottom and closed at the top so that said main section and said subsection are mutually connected only through an upper region of said solvent stripping or regeneration section, a flue plate being arranged under the middle section; said first chamber having an inlet for the crude hydrocarbon mix arranged between said middle section and said separation section of the first chamber and an inlet for solvents which is arranged between said separation or rectification section for non-aromatics and said solvent recovery section of the first chamber; said second chamber having an inlet for a hydrocarbon mix that comprises naphthene and paraffin hydrocarbons in a region between said middle section and said separation section of the second chamber and a second inlet for solvents which is arranged between said paraffin rectification or separation section and said solvent recovery section of the second chamber; and optionally a channel for connection between the head space of the first chamber and said region between said middle section and said separation section of the second chamber for the inflow of head vapors of the chamber containing naphthene and paraffin hydrocarbons. In the column and methods of the invention, an external line can be present for connection between the head space of the first chamber (200) and the region between the middle section (III) and the separation section (II) of the second chamber (300), as an alternative to the internal channel, depending for example on the column size and fed flow rates. For example, an external line can be preferable for big columns while an internal channel can be preferable for a flow rate to be fed in the second chamber being less than 25% of the flow rate fed in the first chamber. The expression "constituted essentially by aromatic, naphthene and paraffin hydrocarbons" referring to the crude hydrocarbon mix indicates that said mix can also contain other hydrocarbons (olefin, diene, acetylene, polyaromatic, . . . ) and/or other compounds (heteroatomic, sulfurated, nitrogenous, oxygenated) at concentrations comprised between 0 and 500 ppm by weight, preferably between 0 and 100 ppm by weight.

In a second aspect, the present invention provides a method for separating and recovering the components of a crude hydrocarbon mix comprising aromatic, naphthene and paraffin hydrocarbons by consecutive extractive distillations, said method comprising the steps of:

a) providing a column for consecutive extractive distillations according to the present invention;

b) feeding said crude hydrocarbon mix into said first chamber through said inlet for the crude hydrocarbon mix, said first chamber being kept within a first preset range of operating temperatures and at a first preset operating pressure;

c) feeding a first extraction solvent into the first chamber through said first solvent inlet;

d) extracting from the lateral rectification subsection of said first chamber an essentially aromatic distillate;

e) sending at least part of the head fraction of the first chamber or a second mix of paraffin and naphthene hydrocarbons obtained by additional separation from at least part of the head vapors of the first chamber to, a region between said middle section and said separation section of the second chamber;

f) feeding into the second chamber a second extraction solvent through said second solvent inlet;

g) extracting from the second chamber a head fraction which essentially comprises paraffin hydrocarbons, preferably with a total content of non-paraffins of less than 1% by weight;

h) extracting from the lateral rectification subsection of said second chamber an essentially naphthene distillate, preferably with a total content of non-naphthenes of less than 1% by weight.

In one embodiment of this method, said column comprises said internal channel which connects the head space of the first chamber and said region between said middle section and said separation section of the second chamber, forming said inlet for a hydrocarbon mix that comprises naphthene and paraffin hydrocarbons in the second chamber, and in step e) at least part of the head fraction of the first chamber is sent directly to the second chamber through said channel. Said channel can be provided in the partition.

The operating temperature in the first chamber is comprised preferably between 30° C. and 300° C., more preferably between 45° C. and 220° C., and the operating pressure is preferably atmospheric or subatmospheric.

Likewise, preferably in the second chamber the operating temperature is comprised between 30° C. and 300° C., more preferably between 45° C. and 220° C., and the operating pressure is preferably atmospheric or subatmospheric.

Moreover, preferably said first solvent and/or said second solvent comprise sulfolane or N-methylpyrrolidone or N-formylmorpholine or tetraethyleneglycol or a mix thereof in a percentage from 99.9% to 80%, preferably from 99.9% to 90%, and water in a percentage from 0.1% to 20%, preferably from 0.1% to 10%.

Finally, the method described above preferably also comprises a step of pre-fractioning of the crude hydrocarbon mix prior to step b) for the separation of C5 and lighter hydrocarbon fractions or for example hydrocarbons with a lower boiling point than n-hexane and/or fractions with a higher number of carbon atoms or a higher boiling point than the hydrocarbons or mixes of interest, for example C7 hydrocarbons and higher or hydrocarbons having a higher boiling point than cyclohexane in order to obtain paraffin and/or naphthene mixes and/or individual paraffin (n-hexane) and/or naphthene (methylcyclopentane, cyclohexane) hydrocarbons of commercial purity.

The invention is illustrated hereinafter with the description of some embodiments, given by way of non-limiting example, with reference to the accompanying drawings, wherein.

Figure 10A:
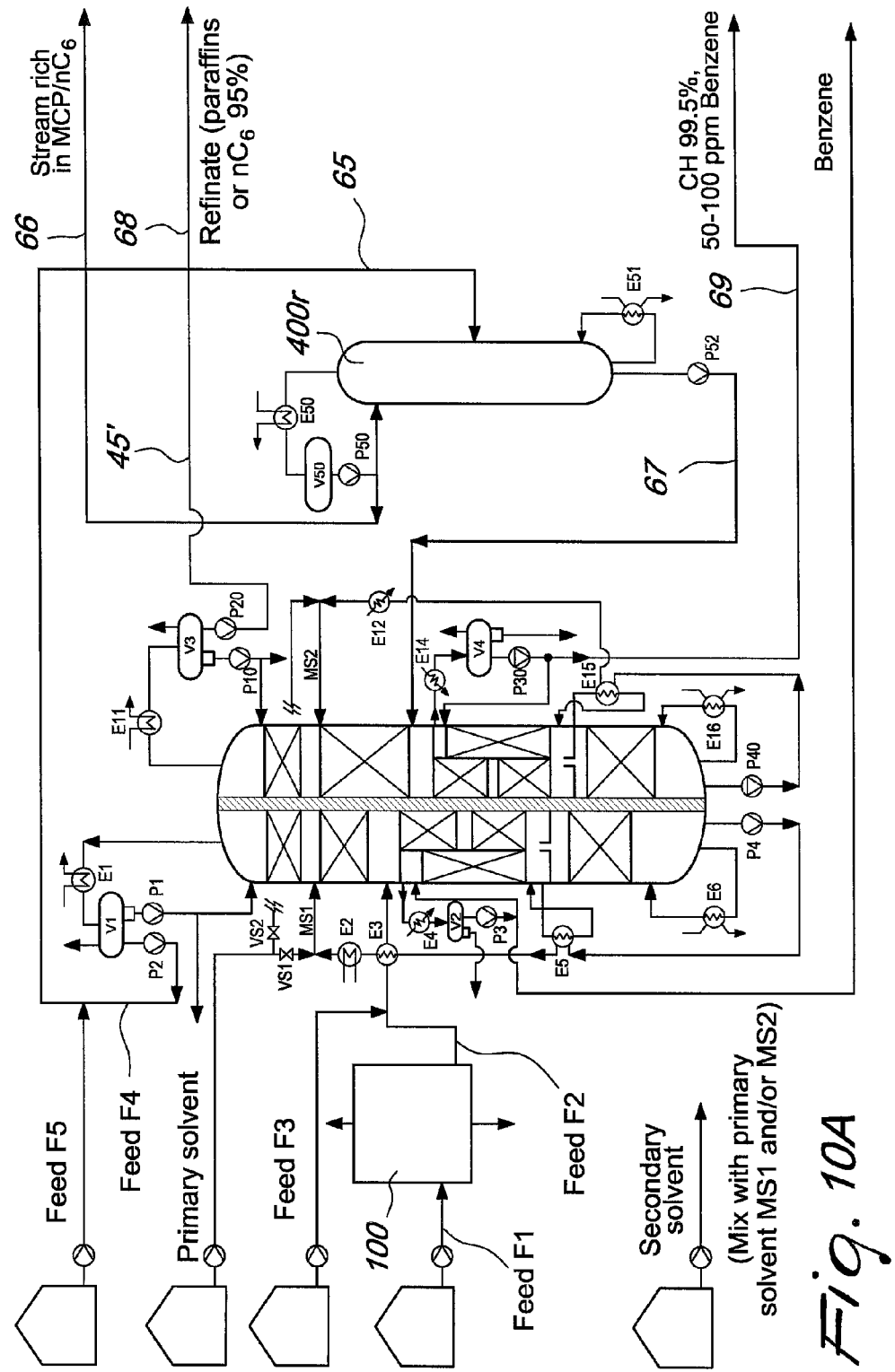
Figure 10B:
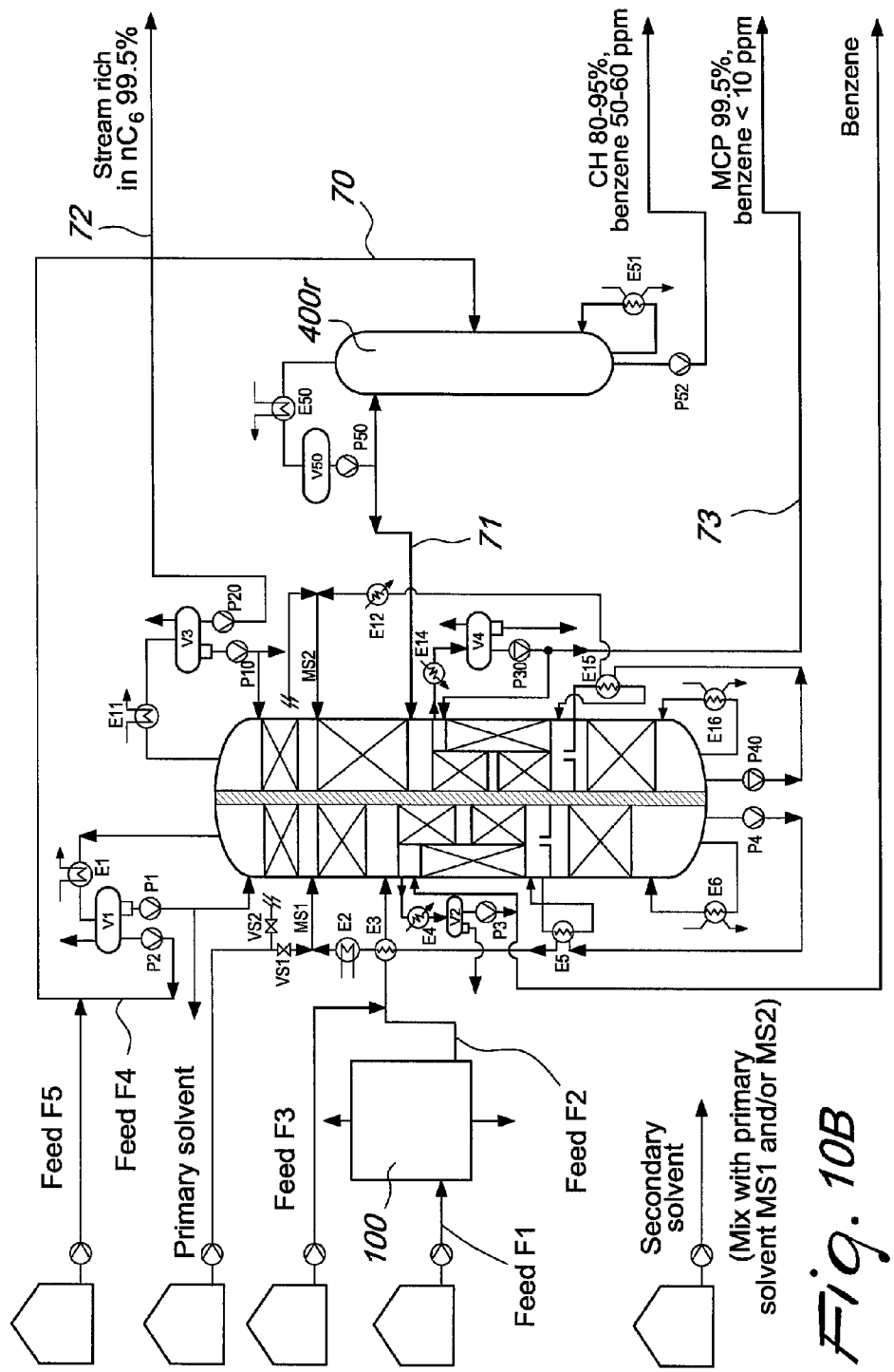
Figure 10C:
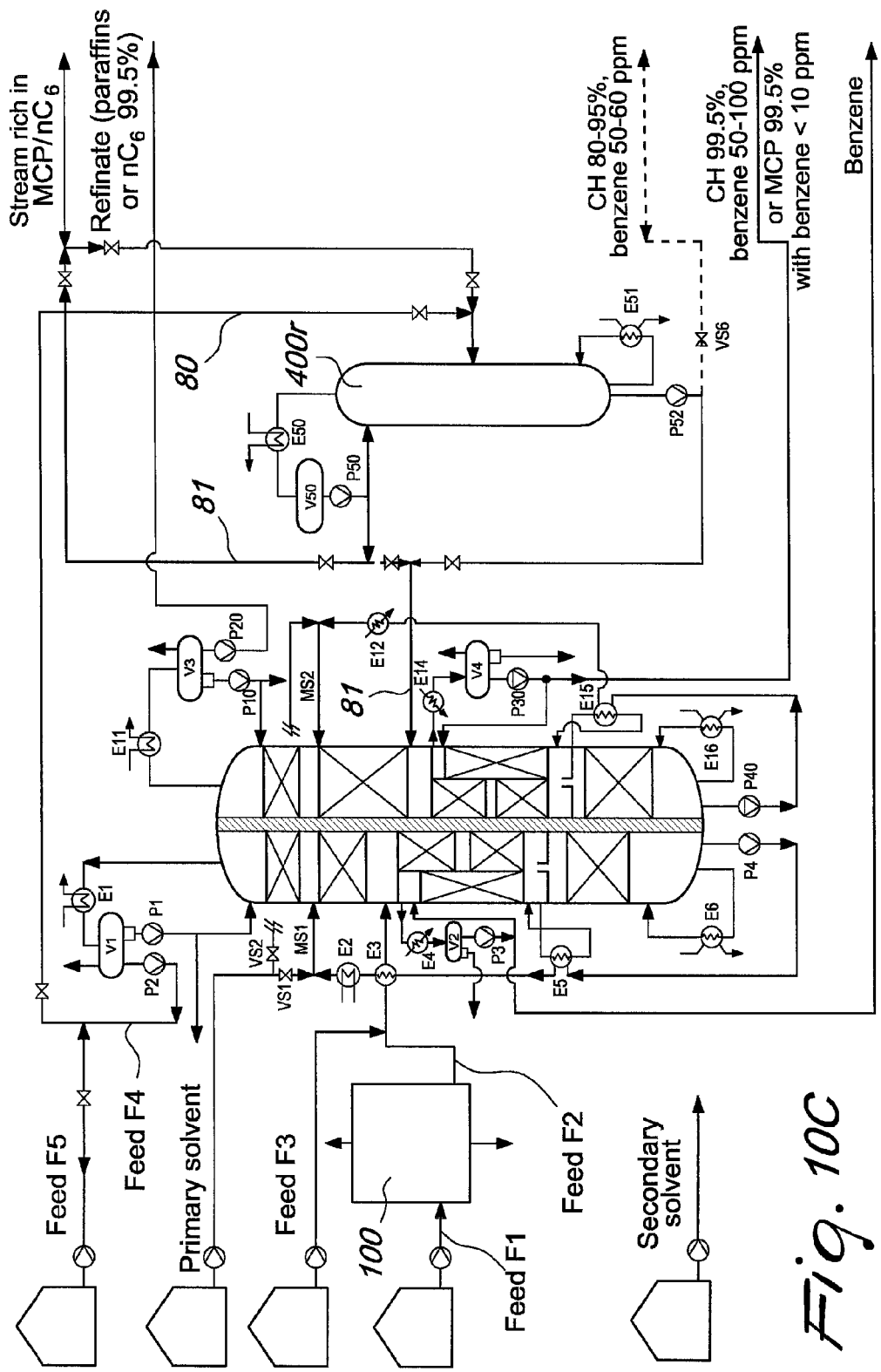
Figure 11:
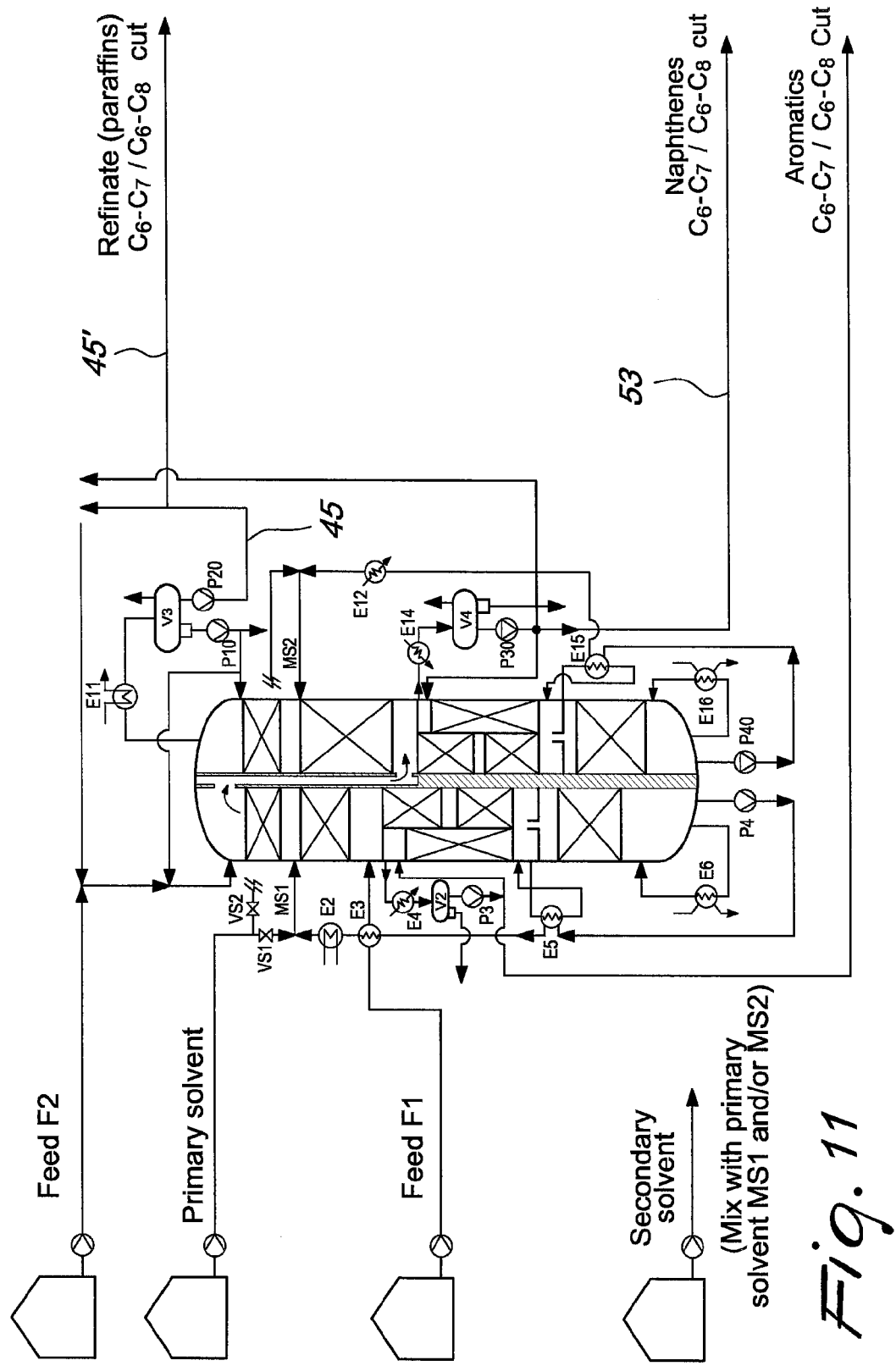
Figure 12:
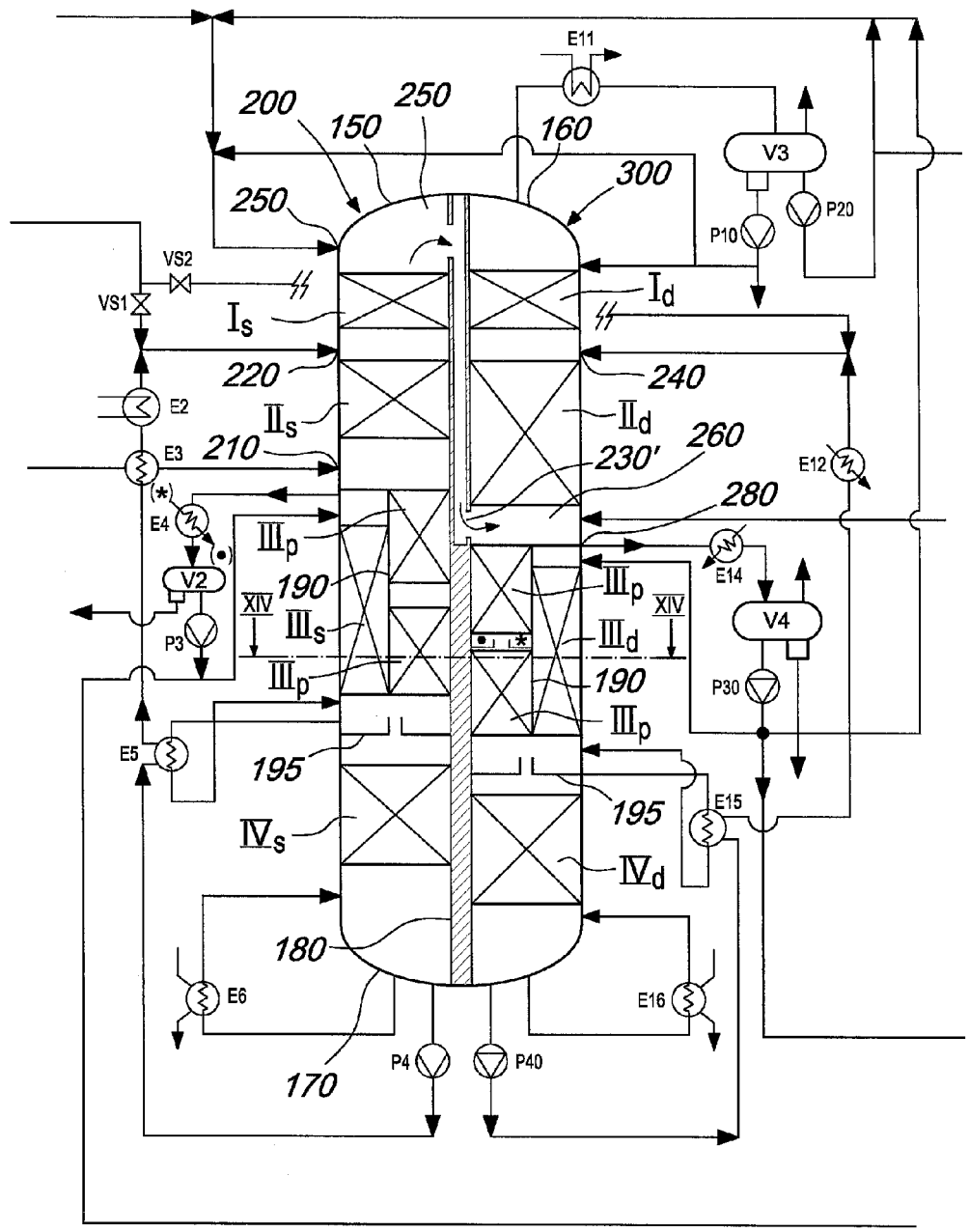
Figure 13:
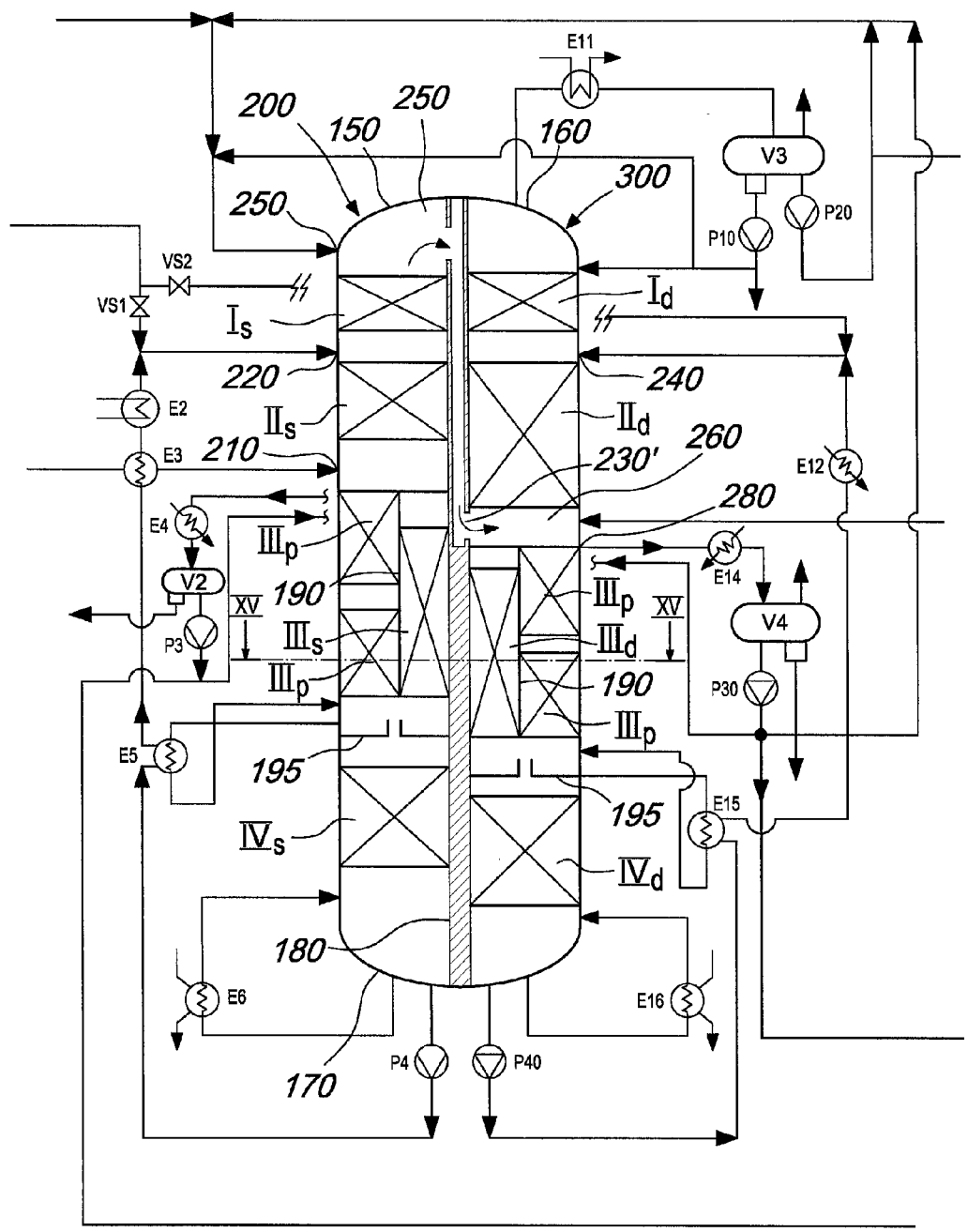
Figure 14:
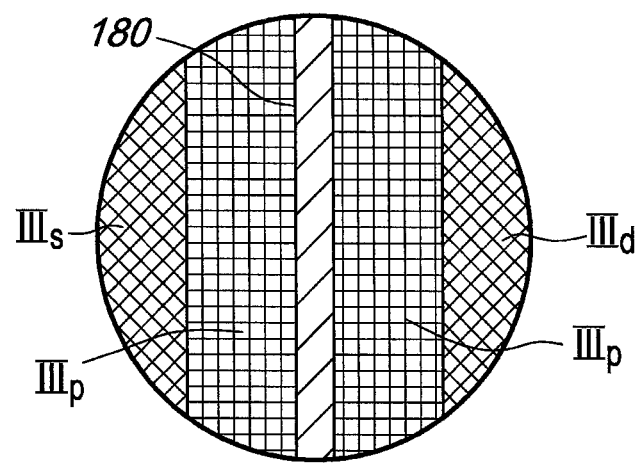
Figure 15:
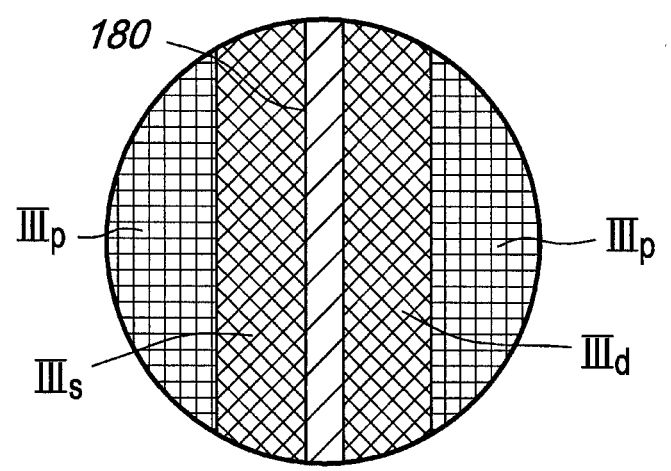
Figure 16:
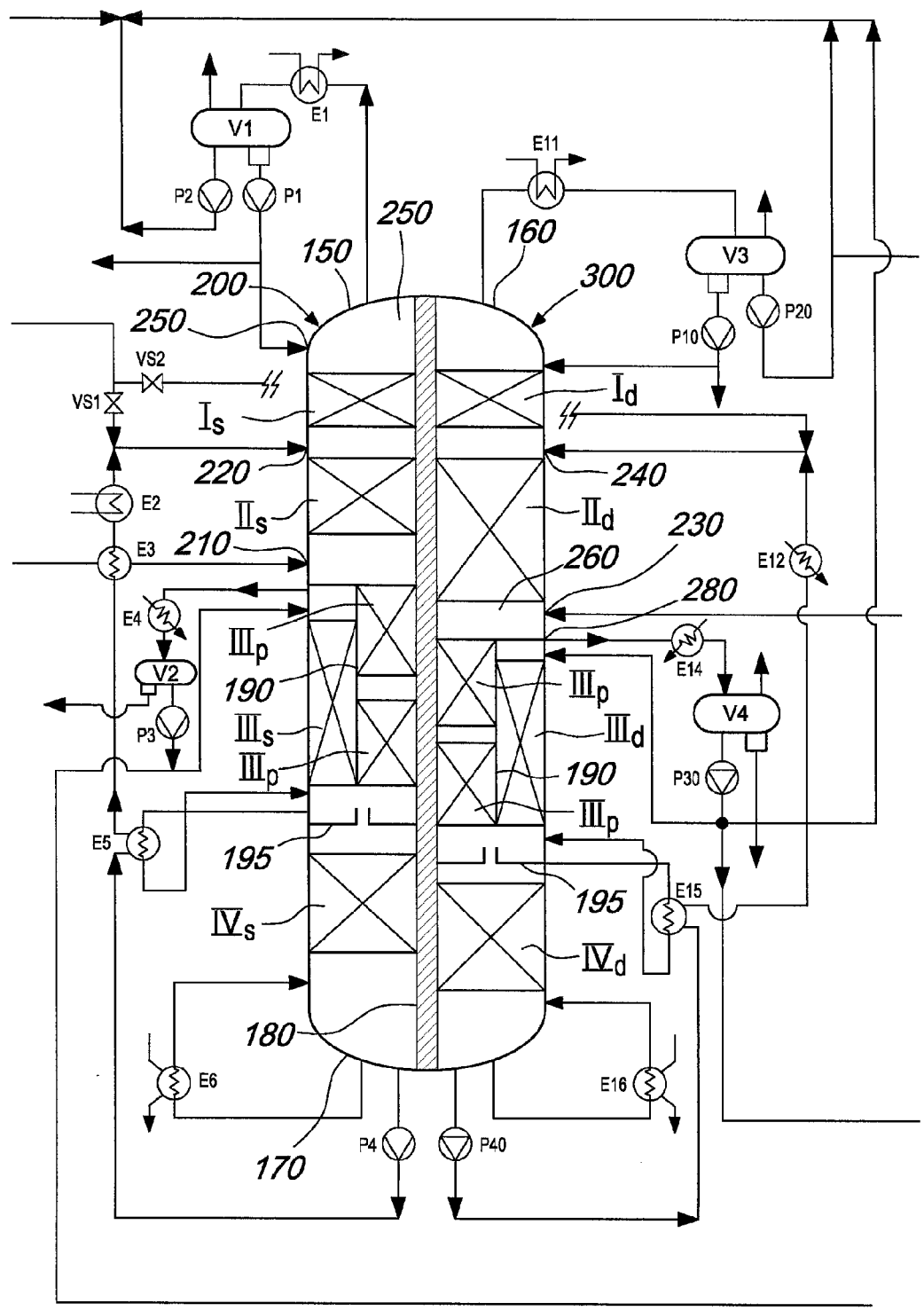
Figure 17:
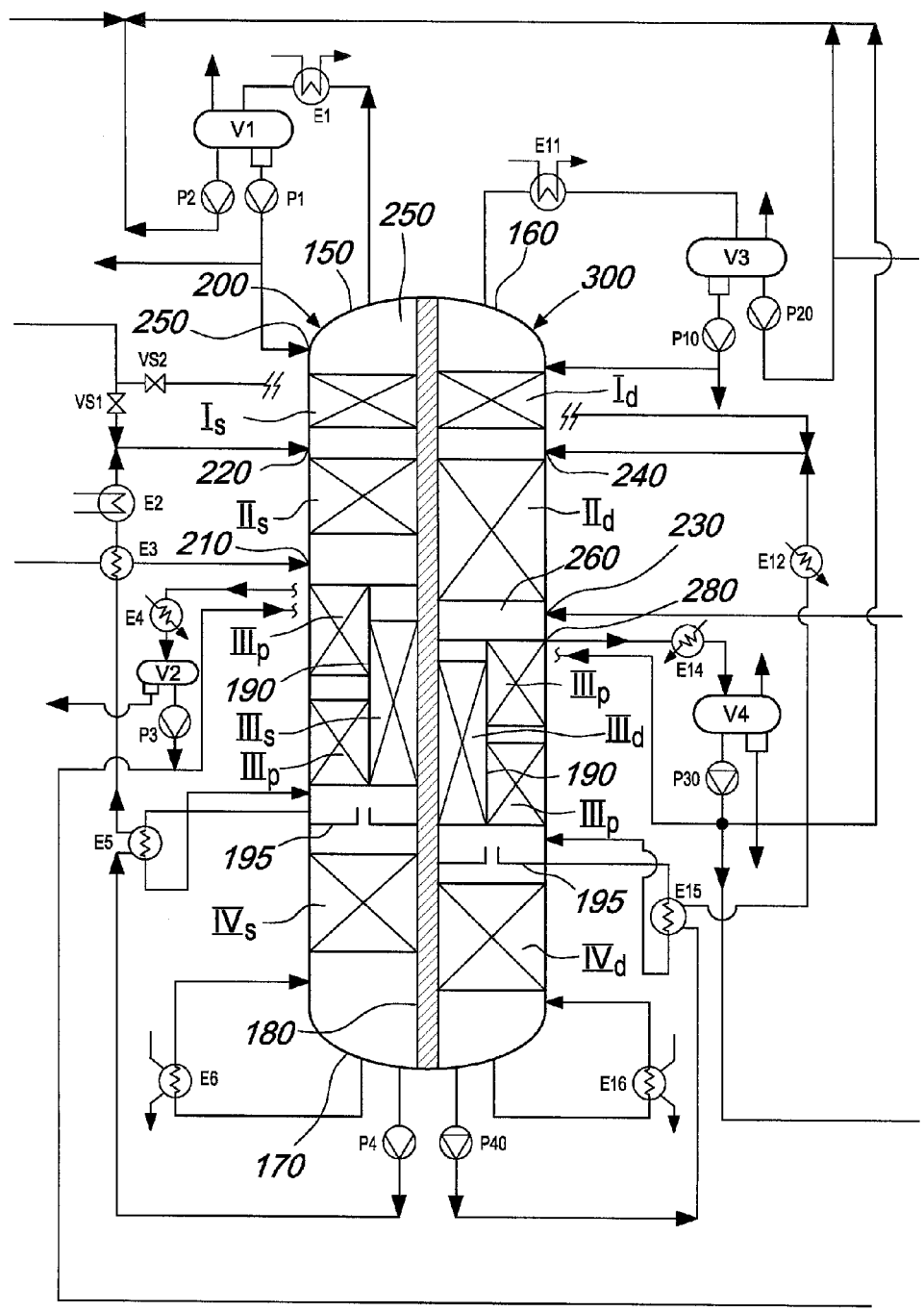

FIG. 10A is a process diagram according to the invention for the production of benzene, cyclohexane and nC6 paraffins, wherein the partition wall of the extractive distillation chambers does not have passage openings inside it for transferring into the second distillation chamber the vapors extracted from the first chamber and accordingly the fractionation of the non-aromatics cut to obtain individual naphthenes/n-paraffins with high purity must be provided upstream of the second extractive distillation chamber;

FIG. 10B is a process diagram according to the invention for the production of benzene, MCP and nC6 with a high titer, in which the partition wall of the extractive distillation chambers does not have passage ports inside it to transfer into the second distillation chamber the vapors extracted from the first chamber and accordingly the fractionation of the non-aromatics cut to obtain individual naphthenes/n-paraffins with high purity must be provided upstream of the second extractive distillation chamber;

FIG. 10C is a process diagram according to the invention for the production of benzene and cyclohexane or MCP, nC6 95% or nC6 99.5%, according to the diagrams 10A and 10B cited above, which provides for optional campaign operation of the unit: this can be helpful if the quantity of non-aromatics in the charge is limited, so as not to allow adequate utilization of the second extractive distillation chamber;

FIG. 11 is a process diagram according to the invention for the production of mixes of pure BT or BTX aromatics, mixes of C6-C7 or C6-C8 naphthenes and mixes of C6-C7 or C6-C8 cut paraffins;

FIG. 12 is an exemplifying but non-limiting diagram of a constructive type of the column partitioned internally with a channel for direct feeding of the head vapors of the left chamber to the right chamber, which can be used for consecutive extractive distillations, wherein the various steps (I left/right, II left/right, III left/right, III sub left and III sub right, IV left/right) can have mutually different difficulties and therefore require a mutually different number of equivalent plates (which can be obtained with valve plates or plates of another type or with fillings and preferably with fillings of the structured type); moreover, the passage section required for each right or left step may also be different;

FIG. 13 is an exemplary alternative of the constructive type of column partitioned internally of FIG. 12;

FIG. 14 is a view of the column in cross section, along the line XIV-XIV of FIG. 12;

FIG. 15 is a view of the column in cross section, along the line XV-XV of FIG. 13;

FIG. 16 shows an internally partitioned column without a channel, which can be used for consecutive extractive distillations;

FIG. 17 is an exemplary alternative of the constructive type of column partitioned internally of FIG. 16.

The column for consecutive extractive distillations according to the present invention is shown in FIGS. 12 and 16. Particularly, the column shown in the process diagrams according to FIGS. 9A, 9B and 11 corresponds to the one shown in detail in FIG. 12. The column shown in the process diagrams according to FIGS. 10A, 10B and 10C corresponds to the one shown in detail in FIG. 16. The column comprises a vertical elongated container 150 which is provided with a head or top 160, a bottom 170 and an internal partition wall 180 which extends vertically from the bottom to the head to the bottom of said container and divides its internal volume, forming a first longitudinal chamber 200 and a second longitudinal chamber 300, which are mutually adjacent, inside said column.

Each one of said chambers 200 and 300 comprises at least four sections I, II, III, IV, of which a middle section III, a solvent regeneration section IV arranged below said middle section, a section for separating an affine component II arranged above said middle section, and a section for the recovery of solvent entrained by a less affine fraction I.

The middle section III is divided into a main section IIIp for stripping components that are not affine with the solvent, which is arranged conveniently but not necessarily toward the inside of the column, and a lateral rectification subsection for removing solvent from the affine components (IIIs in the chamber 200 and IIId in the chamber 300), which is arranged conveniently but not necessarily toward the outside of the column as shown in FIGS. 12 and 16.

The main section (IIIp) for stripping components that are not affine with the solvent, can be also arranged toward the outside of the column and the lateral rectification subsection for removing solvent from the affine components (IIIs in the chamber 200 and IIId in the chamber 300), arranged toward the inside of the column, as shown in FIGS. 13 and 17.

The division by means of a vertical partition wall 190 of the middle section, arranged within the middle section III, wherein said main section IIIp is open at the top and at the bottom and said subsection Ms, IIId is open at the bottom and closed at the top so that said main section IIIp and said subsection IIId, IIIs are mutually connected only through an upper region of said solvent stripping or regeneration section IV.

A flue plate 195, PCs, PCd is arranged under the middle section III, IIIp and IIIs/IIId.

The first chamber 200 has an inlet for the crude hydrocarbon mix 210 arranged between the middle section III and the separation section II of the first chamber 200 and an inlet for solvents 220 which is arranged between the separation or rectification section for non-aromatics II and the solvent recovery section I of the first chamber 200.

The second chamber 300 has an inlet 230 for a hydrocarbon mix that comprises naphthene and paraffin hydrocarbons in a region 260 between the middle section III and the separation section II of the second chamber 300, and a second inlet for solvents 240, which is arranged between said paraffin rectification or separation section II and the solvent recovery section I of the second chamber 300.

Figure 9A:
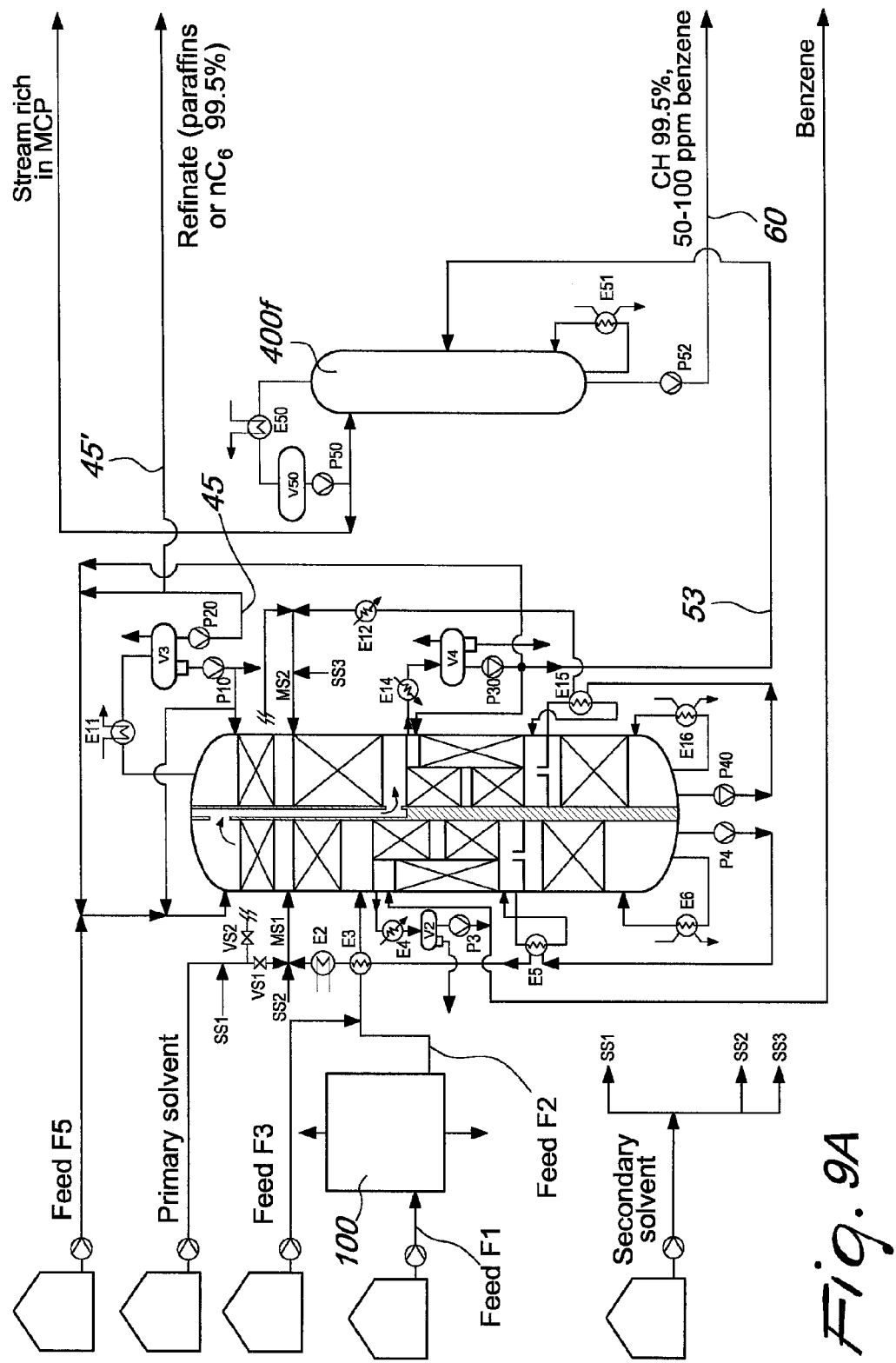
FIG. 9A is a process diagram, according to the preferred embodiment of the invention, for the recovery of benzene, cyclohexane and a stream rich in n-C6.
Figure 9B:
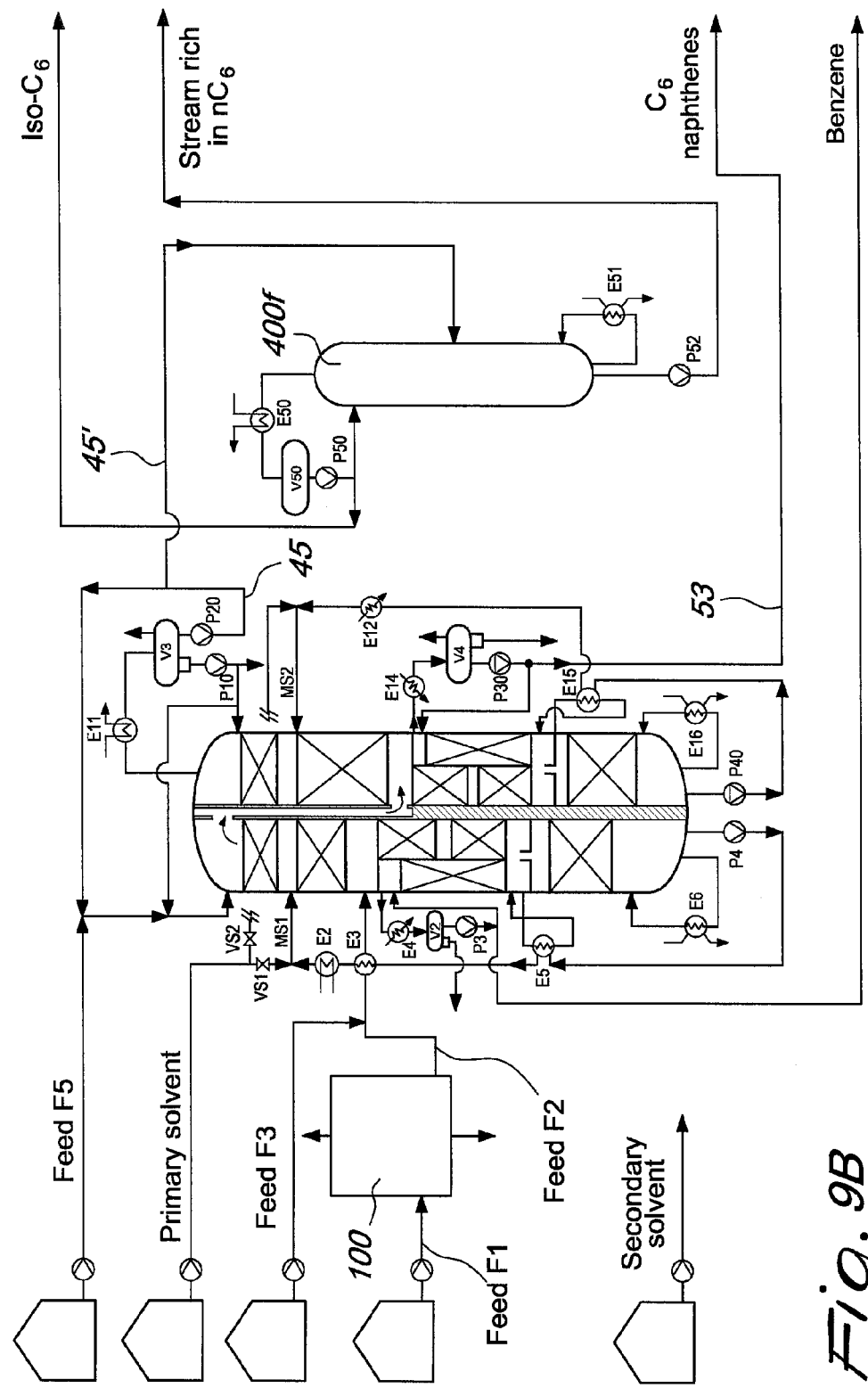
FIG. 9B is a process diagram according to the preferred embodiment of the invention for the recovery of benzenes, C6 naphthenes, C6 iso-paraffins and a stream rich in n-C6.

In a first embodiment, shown in FIG. 12 and also in FIGS. 9A and 9B, there is a channel 270 for connection between the head space 250 of the first chamber 200 and the region 260 between the middle section III and the separation section II of the second chamber 300, for the inflow of head vapors of the chamber 200 containing naphthene and paraffin hydrocarbons. The channel 270 can be provided for example inside the partition 180.

In a second embodiment of the column for consecutive extractive distillations of the present invention, shown in FIG. 13 and also in FIGS. 10A-10C, the first chamber 200 and the second chamber 300 are not mutually connected. For example, the partition 180 is continuous, without openings, and allows complete separation between the first chamber 200 and the second chamber 300.

The method according to the present invention for separating and recovering the components of a crude hydrocarbon mix comprising aromatic, naphthene and paraffin hydrocarbons by consecutive extractive distillations is performed by using the column for consecutive extractive distillations of the present invention, in particular according to the first or second embodiments described above.

The process of the present invention comprises the steps of:

a) providing a column for consecutive extractive distillations according to the present invention;

b) feeding the crude hydrocarbon mix into the first chamber 200 through the inlet 210 for the crude hydrocarbon mix, the first chamber 200 being kept within a first preset range of operating temperatures and at a first preset operating pressure;

c) feeding a first extraction solvent into the first chamber 200 through said first solvent inlet 220;

d) extracting from the lateral rectification subsection IIIs of said first chamber 200 an essentially aromatic distillate;

e) sending at least part of the head fraction of the first chamber 200 or a second mix of paraffin and naphthene hydrocarbons obtained by additional separation from at least part of the head vapors of the first chamber, to a region 260 between the middle section III and the separation section II of the second chamber 300;

f) feeding into the second chamber 300 a second extraction solvent through said second solvent inlet 240;

g) extracting from the second chamber 300 a head fraction which essentially comprises paraffin hydrocarbons, preferably with a total content of non-paraffins of less than 1% by weight;

h) extracting from the lateral rectification subsection IIId of said second chamber an essentially naphthene distillate, preferably with a total content of non-naphthenes of less than 1% by weight.

In a first embodiment, shown in FIGS. 9A and 9B, at least one part of the head fraction of the first chamber 200, through the channel 170, enters from the inlet 230 into the region 260 between the middle section III and the separation section II of the second chamber 300.

With reference to FIG. 9A, the naphthene distillate of step h, or parts thereof (stream 53) can be sent to a fractionation column 400*f*, where a stream substantially of cyclohexane (99.5% by weight of cyclohexane, 50-100 ppm benzene) and a stream 60 rich in methylcyclopentane are separated.

With reference to FIG. 9B, the paraffin fraction of step g) or part thereof (stream 45') can be sent to a fractionation column 400*f*, where a stream rich in n-hexane and a stream reach in iso-hexanes are separated.

In a second embodiment, shown in FIGS. 10A-10C, a second mix of paraffin and naphthene hydrocarbons obtained by further separation from at least part of the head vapors of the first chamber enters from the inlet 230 for a hydrocarbon mix comprising naphthene and paraffin hydrocarbons.

In this case, the method cited above can provide, in step e), for at least part of the head fraction of the chamber 200 to be sent to a separation column, where a second mix of paraffin and naphthene hydrocarbons is separated.

In an alternative, as shown in FIG. 10A, in step e) at least one part of the head fraction of the chamber 200 (stream 65) can be sent to a rectification column 400*r* so as to separate a head fraction, which contains the naphthenes that are lighter than cyclohexane (stream 66) from a bottom fraction (stream 67), which essentially comprises C6 normal paraffins and cyclohexane, the bottom fraction being sent to the upper part of the main stripping section IIIp of the second chamber 300, through the inlet 230 for hydrocarbon mix comprising naphthene and paraffin hydrocarbons, and wherein a stream 68 substantially of n-hexane is extracted from the head of the second chamber 300 (the purity, which is >95% by weight, being determined by the presence of 2,2-dimethylpentane in the charge), and a stream 69 substantially of cyclohexane (i.e., purity >99.5% by weight, 50-100 ppm benzene) is extracted from the lateral rectification subsection IIId of said second chamber 300.

In a second alternative, shown in FIG. 10B, in step e) at least one part of the head fraction of the chamber 200 (current 70) can be sent to a rectification column (400*r*) so as to separate a head fraction that is practically free from cyclohexane from crude cyclohexane produced as a bottom product (purity 80-95%), said head fraction comprising essentially C6 normal paraffins and methylcyclopentane and being sent (stream 71) to the upper part of the main stripping section IIIp of the second chamber 300 through the inlet (230) for a hydrocarbon mix that comprises naphthene and paraffin hydrocarbons, and wherein a stream 72 substantially of n-hexane (purity >99.5%) is extracted from the head of the second chamber and a stream 73 substantially of methylcyclopentane (purity >99.5%) is extracted from the lateral rectification subsection IIId of said second chamber.

In a further alternative of the method cited above, shown in FIG. 10C, at least part of the head fraction of the column 200 (stream 80) can be sent to a rectification column 400*r* so as to separate a mix that comprises predominantly n-hexane and methylcyclopentane, which is partly sent to the upper part of the main stripping section IIIp of the second chamber 300 and is partly (stream 81) collected for storage. The three high-purity products n-C6, MCP and CE can be obtained with campaign runs of the column 400*r* and of the chamber 300 of the extractive distillation column.

In a third aspect, the present invention relates to a method for separating and recovering the components of a crude hydrocarbon mix comprising aromatic, naphthene and paraffin hydrocarbons, said method comprising the steps of:

a) providing a column for consecutive extractive distillations of the present invention according to what has been described previously;

b) feeding said crude hydrocarbon mix into the first chamber 200, said chamber being kept in a first preset range of operating temperatures and at a first preset operating pressure;

c) feeding a first mix of extraction solvents into the first chamber 200 in a region that lies above the feeding region of said crude mix, wherein said mix of extraction solvents comprises sulfolane, or N-methylpyrrolidone, or N-formylmorpholine, or tetraethyleneglycol or mixes thereof, and optionally water as a cosolvent;

d) feeding to the head of the first chamber 200 a liquid reflux mix having a preset composition and comprising water and hydrocarbons, wherein said mix is essentially without aromatic hydrocarbons; said mix can be obtained as a head product of the first chamber 200 after condensation of extracted vapors and separation of the aqueous phase from the hydrocarbon phase or it can originate from external storage/purchases/transfers or it can originate from the head of the second chamber and be essentially aqueous or essentially paraffin or it can originate from part of the head of the first chamber 200 and part of the head of the lateral rectification subsection of the second chamber IIId of the naphthene phase;

e) extracting from the head of the first chamber 200 a first fraction of head vapors comprising essentially non-aromatic hydrocarbons and optionally water;

f) extracting from the lateral rectification subsection of the first chamber IIIs an essentially aromatic distillate in the vapor phase which is condensed and optionally at least partially sent to further treatments, optionally selected from benzene-toluene-xylene fractionation if the aromatic extract is a BTX mix, or to uses of benzene for ethylbenzene, cumene, LAB, cyclohexane via hydrogenation, or others;

g) feeding to the head of the lateral rectification subsection of the first chamber IIIs a liquid reflux mix which comprises essentially aromatic hydrocarbons;

h) extracting, from the flue plate that divides the sections IIIp/IIIs from the section IV, solvent that is rich in aromatics, recirculating it, preferably with natural circulation, in the reboiler E5, from which, after partial vaporization, it is returned into the chamber 200 below the sections IIIp/IIIs;

i) extracting from the bottom of the first chamber 200 a mix that comprises at least one solvent or essentially only the main solvent if the second solvent is water, wherein the term "essentially" is understood to mean that the residual aromatic content is <0.5%, preferably <0.1%, at least a first part of said mix being sent by natural circulation to a thermosyphon reboiler E16 and thus returning to the bottom of the section IV, and a second part of said mix being sent to pumps P4 for recycling of the solvent or solvents, said mix being extracted from the bottom of the first chamber 200 in at least two different extraction lines, or in a single line that is divided into at least two other lines for said first part and said second part of the mix, and then returning to the bottom of the section IV, without aromatic hydrocarbons;

l) feeding to the head of the section II of the first chamber 200 the mix obtained in the last extraction of step h), conveniently cooled with release of heat into the reboiler E5, into the preheater of the charge E3 and into the final coolant E2;

m) sending to the second chamber 300 at least part of the head fraction of step e), optionally after fractionation;

n) feeding into the chamber 300, at the top of the section II, in a region that lies above the region for feeding the mix to step l), an extraction mix which comprises the same components as the mix in step c), with an optional variation of the ratio between main solvent and water, if present;

o) feeding to the head of the chamber 300 a liquid reflux mix having a preset composition and comprising water and/or paraffin hydrocarbons, wherein said mix is essentially free from naphthene hydrocarbons (content <0.5%, preferably <0.1%) and originates from the head vapors of the second chamber 300 after condensation and separation of the aqueous phase from the paraffin phase, optionally partly recombined to constitute the reflux;

p) extracting from the second chamber 300 a fraction of head vapors which comprises essentially paraffin hydrocarbons, which is condensed with the separation of paraffin hydrocarbons and of any water, and optionally sent, at least partially, to further possible treatments, optionally the paraffin fraction being distilled for separation of N-hexane from iso-hexanes or being separated by adsorption/desorption on 5-angstrom molecular sieves; or used to produce ethylene by S/cracking;

q) extracting from the lateral rectification subsection of the second chamber IIId an essentially naphthene distillate in the vapor phase, which is condensed and optionally at least partially sent to further treatments;

r) feeding to the head of the lateral rectification subsection of the second chamber IIId a liquid mix which comprises essentially naphthene hydrocarbons;

s) extracting from the bottom of the second chamber 300 a mix comprising at least one solvent, or essentially only the main solvent if the second solvent is water, wherein the term "essentially" is understood to mean that the residual naphthene content is <0.5%, preferably <0.1%, at least a first part of said mix being sent by natural circulation to a thermosyphon reboiler E16 and then returning to the bottom of the section IV, and a second part of said mix being sent to pumps P40 for recycling the solvent or solvents, said mix being extracted from the bottom of the second chamber 300 in at least two different extraction lines or in a single line that is divided into at least two other lines for said first part and said second part of the mix and then returns to the bottom of the section IV without naphthene hydrocarbons;

t) feeding to the head of the section II of the second chamber 300 the mix obtained in the last extraction of step s), conveniently cooled by transfer of heat in the reboiler E15 (optionally in an external preheater of the charge, which is not shown) and in the final coolant E12.

In an embodiment of this last described aspect, in step m) the at least one part of the head fraction of step e) is sent to the second chamber 300 through said channel which is inside the column for consecutive extractive distillations, connecting the head of the first chamber 200 to the upper part of the main stripping section IIIp of the second chamber 300.

In the column and methods of the invention, an external line can be present for connection between the head space of the first chamber (200) and the region between the middle section (III) and the separation section (II) of the second chamber (300), as an alternative to the internal channel, depending for example on the column size and fed flow rates. For example, an external line can be preferable for big columns while an internal channel can be preferable for a flow rate to be fed in the second chamber being less than 25% of the flow rate fed in the first chamber.

Preferably, said crude hydrocarbon mix is, for example, the one in Table 9 wherein benzene, cyclohexane and/or methylcyclopentane and/or n-hexane are separated and the liquid distillate of step p) is fed to a fractionation column 400f, in which a naphthene component, preferably cyclohexane, is separated at the head and/or the bottom.

It is also preferable for said crude hydrocarbon mix to be, for example, the one given in Table 6, in which benzene, a stream of C6 naphthenes constituted by cyclohexane and/or methylcyclopentane and a stream of C6 paraffins and/or n-hexane are separated and in which the liquid distillate of step o) is fed to a fractionation column in which a paraffin component of commercial purity, preferably n-hexane, is separated at the head and/or the bottom.

In another embodiment of the last aspect described for the obtainment of benzene and cyclohexane, said crude hydrocarbon mix is, for example, the one in Table 9, wherein in step m) the at least one part of the head fraction of step e) is sent to a rectification column (400r) from which a mix is obtained which comprises predominantly paraffins and cyclohexane and is sent to the second chamber (300) above the main stripping section (IIIp).

In another embodiment of the last aspect described for obtaining benzene, a stream rich in n-hexane and methylcyclopentane, said crude hydrocarbon mix is, for example, the one in Table 5 and in step m) the at least one part of the head fraction of step e) is sent to a rectification column 400r from which one obtains at the head a mix that comprises predominantly n-hexane and methylcyclopentane and is sent to the second chamber 300 above the main stripping section IIIp.

Preferably, the liquid reflux mix of step d) comprises the aqueous phase that originates from the separation of the condensate of step p) or the paraffin hydrocarbons that originate from the separation of step p) or it comprises a part of the paraffin hydrocarbons that originate from the separation of the condensate of step p) and at least one part of the naphthene mix of step q).

TABLE 5

| Components of the mix | % by weight | Boiling point (° F.) |
|---|---|---|
| 2,2-Dimethylbutane | 0.1 | 136.4 |
| 3-Methylpentane | 5.3 | 146 |
| n-Hexane | 19.3 | 155.7 |
| Methylcyclopentane | 51.6 | 161.3 |
| Benzene | 15.5 | 176.2 |
| Cyclohexane | 8.2 | 177.3 |

TABLE 6

| Hydrocarbon | Percentage by volume |
|---|---|
| 2-Methylpentane | 7.1 |
| 3-Methylpentane | 10.1 |
| n-Hexane | 49.5 |

TABLE 6-continued

| Hydrocarbon | Percentage by volume |
| --- | --- |
| Methylcyclopentane | 14.1 |
| Cyclohexane | 15.2 |
| Benzene | 3.5 |
| 2,4-Dimethylpentane | 0.5 |

TABLE 7

Typical composition of a naphtha mix containing 10% by weight of aromatics

| Component | % by weight |
| --- | --- |
| n-Butane | 1.5 |
| i-Pentane | 4.2 |
| n-Pentane | 10.3 |
| Cyclopentane | 1.5 |
| 2,3-Dimethylbutane | 0.8 |
| 2-Methylpentane | 6.0 |
| 3-Methylpentane | 4.0 |
| n-Hexane | 8.6 |
| Me-cyclopentane | 4.1 |
| Benzene | 1.8 |
| Cyclohexane | 2.8 |
| 2-Methylhexane | 2.8 |
| 3-Methylhexane | 3.8 |
| n-Heptane | 4.4 |
| Methylcyclohexane | 4.8 |
| Toluene | 3.0 |
| 2-Methylheptane | 2.4 |
| 1,3-Dimecyclohexane | 7.0 |
| n-octane | 5.4 |
| Ethylcyclohexane | 2.0 |
| 2,6-dimethylheptane | 1.9 |
| Ethylbenzene | 2.0 |
| p-xylene | 1.9 |
| 3-Methyloctane | 2.7 |
| o-xylene | 1.0 |
| n-nonane | 2.6 |
| n-decane | 3.0 |
| i-decanes | 4.0 |
| TOTAL | 100.3 |

TABLE 8

| Hydrocarbon | Boiling point at 760 mm ° C. |
| --- | --- |
| Normal hexane | 68.740 |
| Methylcyclopentane | 71.812 |
| 2,2-dimethylpentane | 79.197 |
| Benzene | 80.100 |
| 2,4-Dimethylpentane | 80.500 |
| Cyclohexane | 80.738 |
| 2,2,3-trimethylpentane | 80.882 |
| 3,3-dimethylpentane | 86.064 |
| 1,1-dimethylcyclopentane | 87.846 |
| 2,3-dimethylpentane | 89.784 |
| 2-methylhexane | 90.052 |
| 1,trans-3-dimethylcyclopentane | 90.773 |
| 1,cis-3-dimethylcyclopentane | 91.725 |
| 3-methylhexane | 91.850 |
| 1,trans-2-dimethylcyclopentane | 91.869 |

TABLE 9

| Hydrocarbon | Percentage by volume |
| --- | --- |
| Components with low boiling point | Traces |
| Normal hexane | 37.0 |
| Methylcyclopentane | 30.1 |

TABLE 9-continued

| Hydrocarbon | Percentage by volume |
| --- | --- |
| 2,2-dimethylpentane | 2.2 |
| Benzene | 9.9 |
| 2,4-Dimethylpentane | 1.3 |
| Cyclohexane | 19.5 |
| Components with high boiling point | Traces |
| TOTAL | 100 |

The invention can be applied to C6 cuts optionally extended to C5 to recover cyclopentane, C6-C7, C6-C8, C6-C9, C6-C9+, desulfurated naphthas, condensates, NGL, reformates from continuous or semiregenerative or cyclic reforming (CCR) of naphthas of different origin and distillation range, i.e., pyrolysis gasolines.

Figure 1:
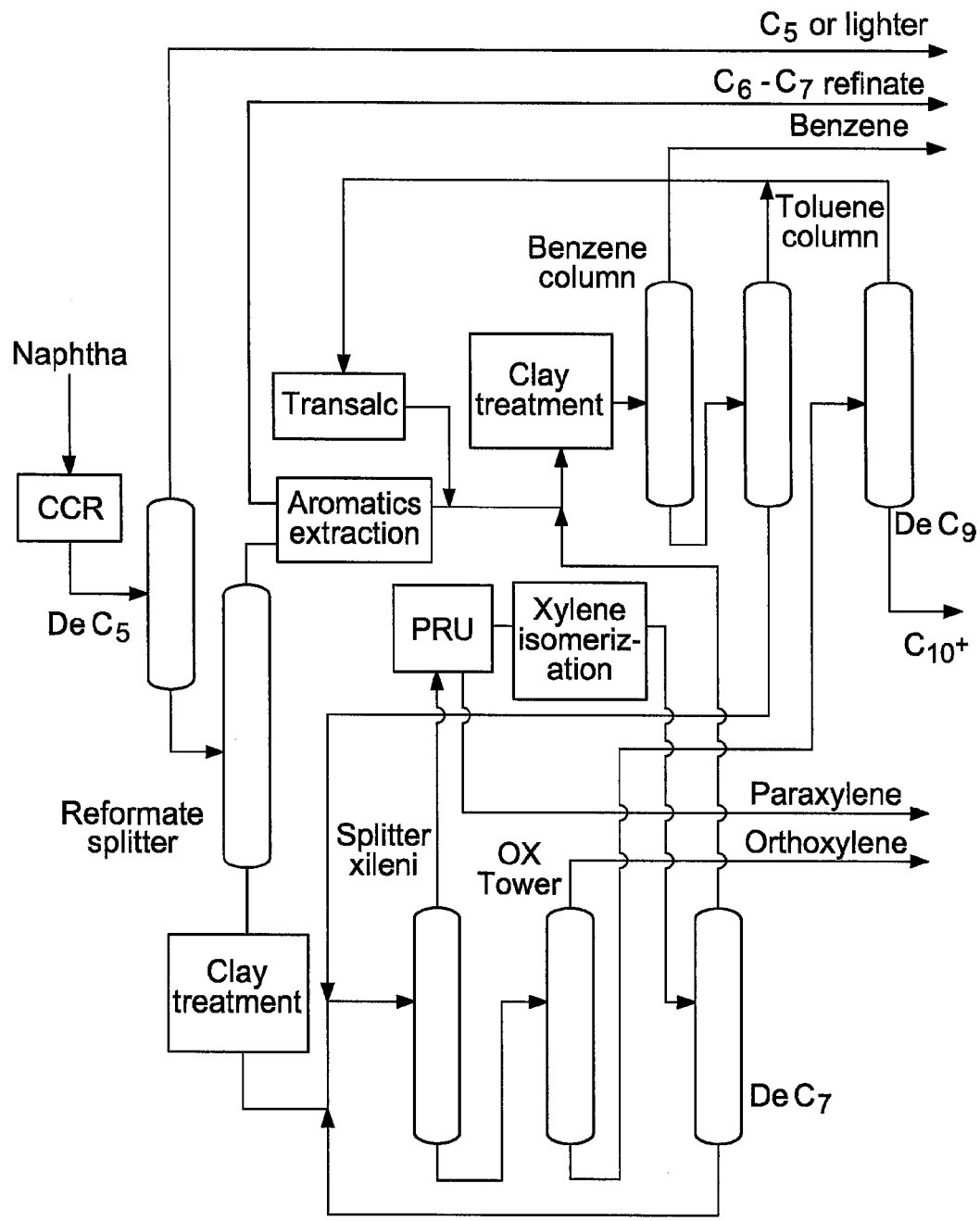
FIG. 1 is a process diagram of an "aromatics complex" according to the background art.
Figure 2:
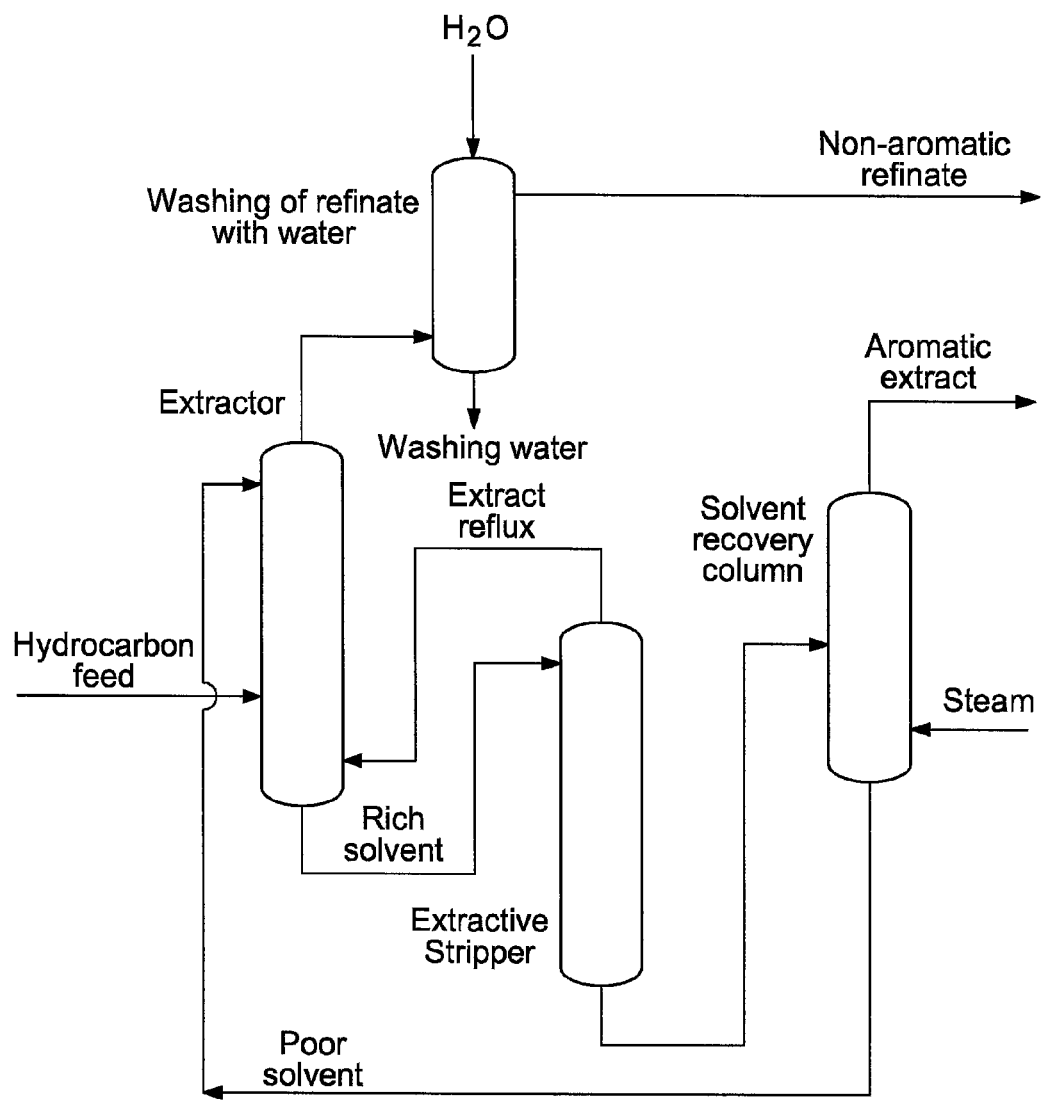
FIG. 2 is a process diagram of a base unit for the extraction of aromatics according to the background art.
Figure 3:
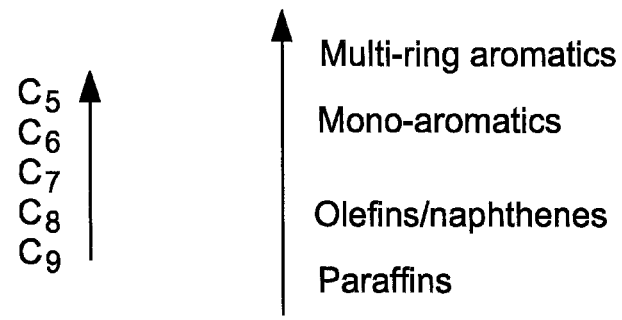
FIG. 3 illustrates the selectivity of the solvent to petrochemical hydrocarbons.
Figure 5:
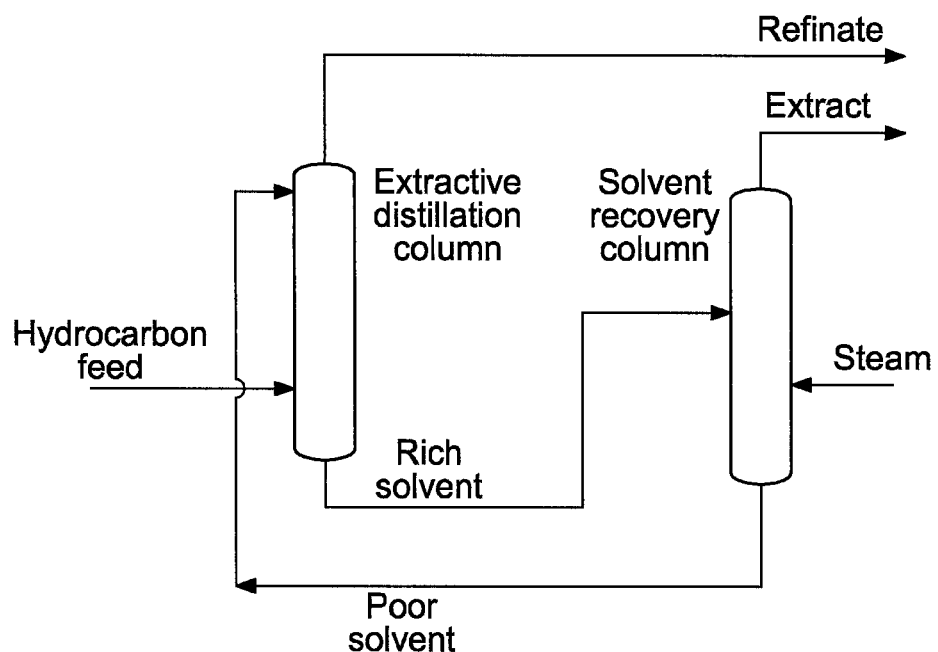
FIG. 5 is a process diagram of a system of extractive distillation for the recovery of aromatics according to the background art.
Figure 4:
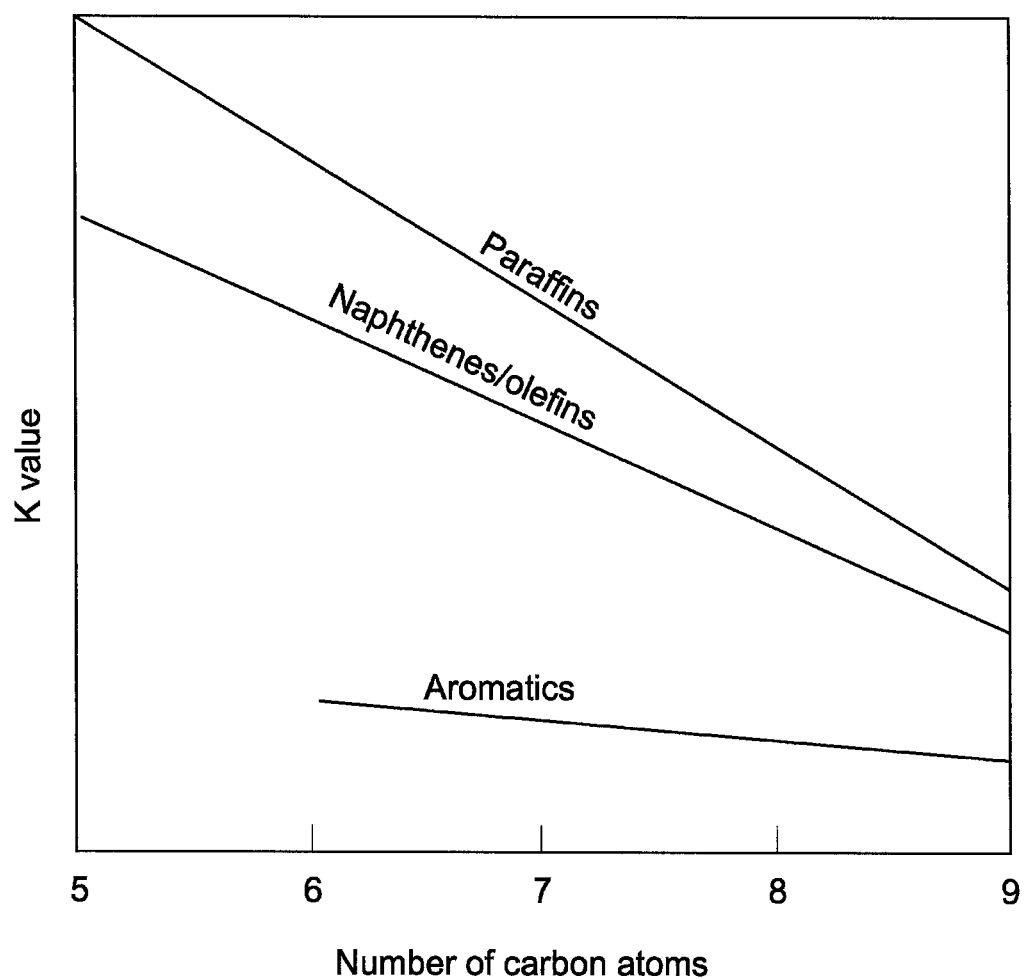
FIG. 4 shows the relative effect of polar solvents on the hydrocarbon species.
Figure 6:
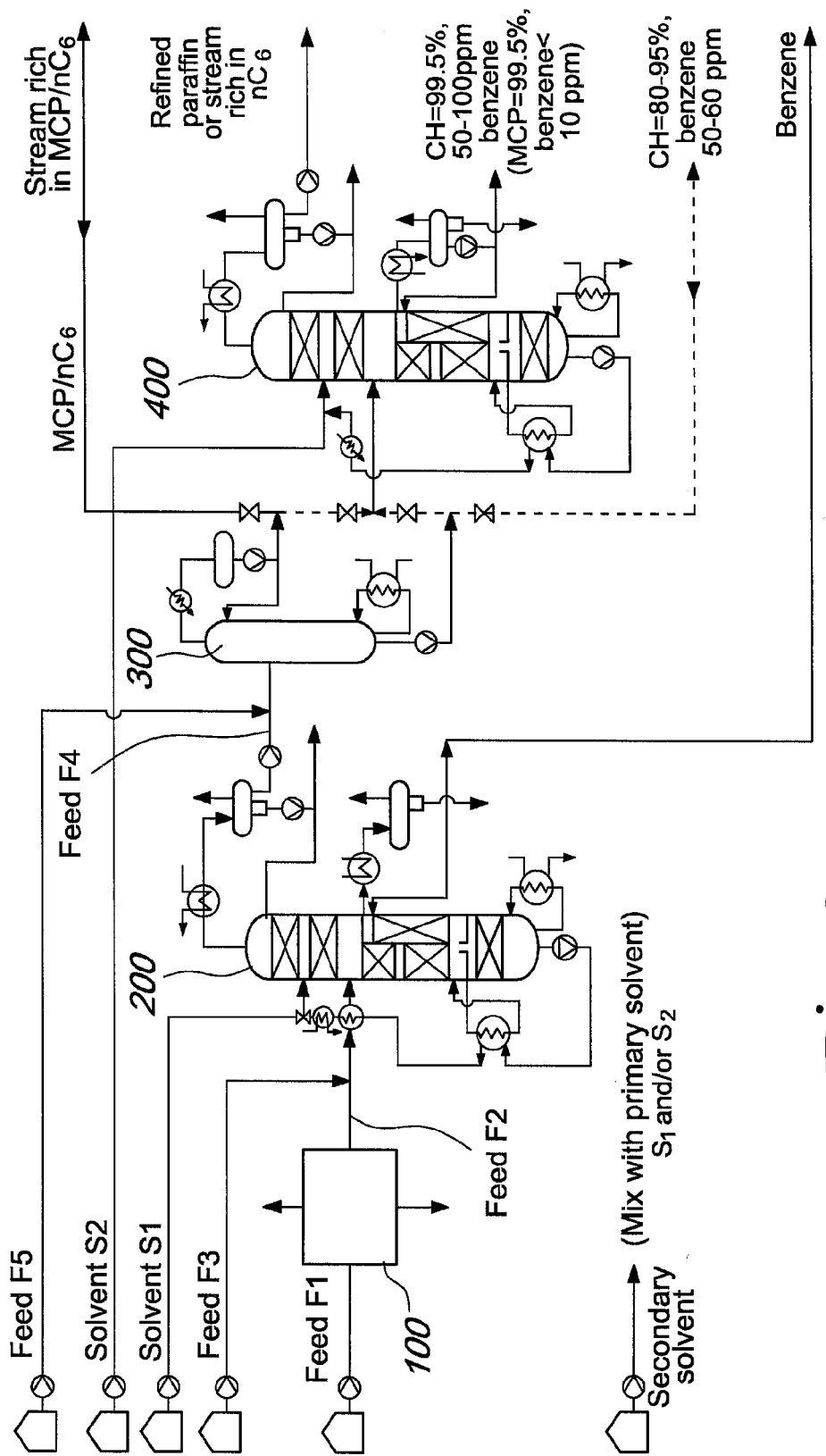
FIG. 6 is a process diagram for the production of benzene and cyclohexane or of benzene, n-hexane and methylcyclopentane according to the background art.
Figure 7:
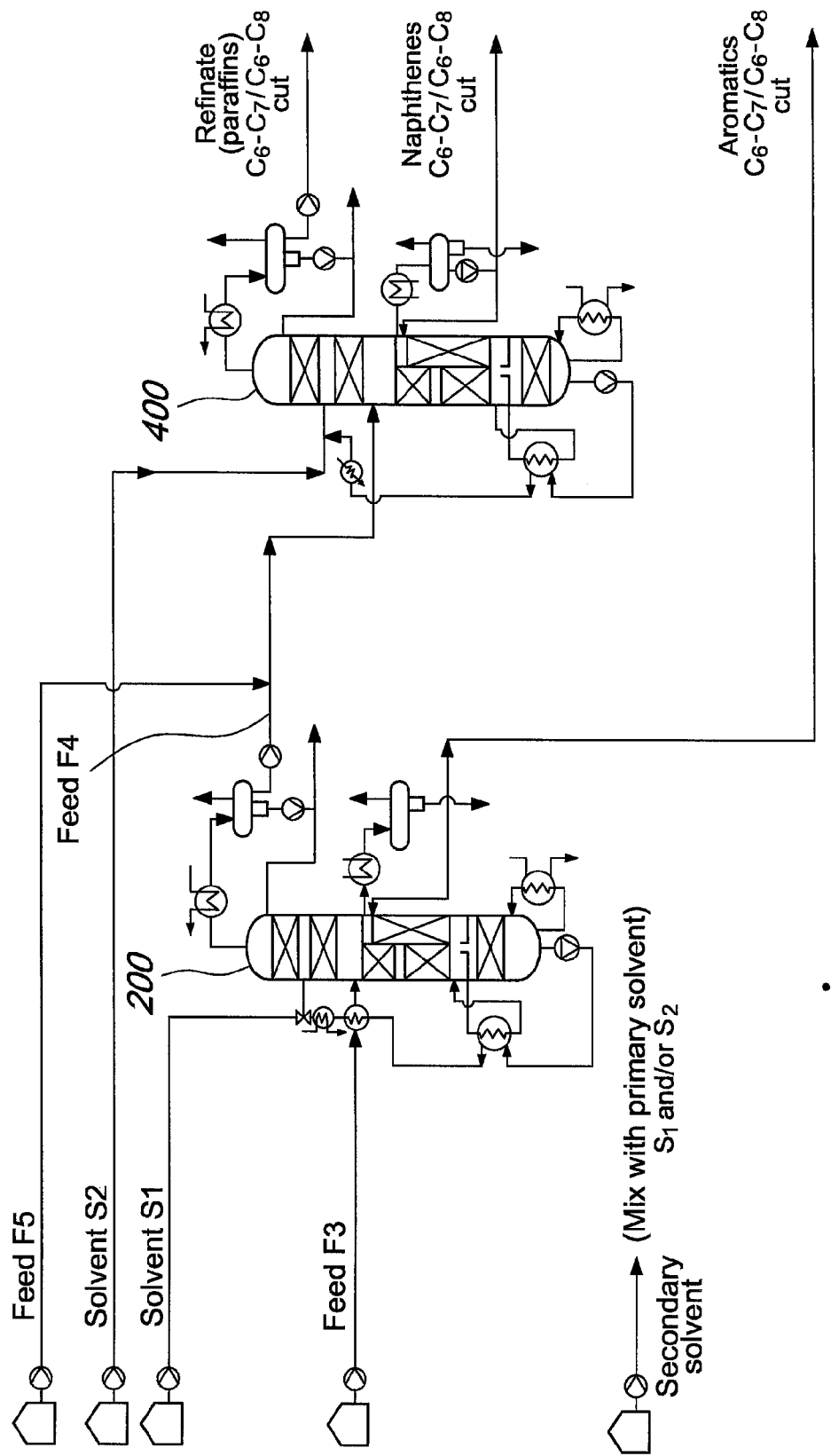
FIG. 7 is a process diagram for the simultaneous production of C6-C7 cut or C6-C8 cut aromatics, paraffins and naphthenes according to the background art.
Figure 8:
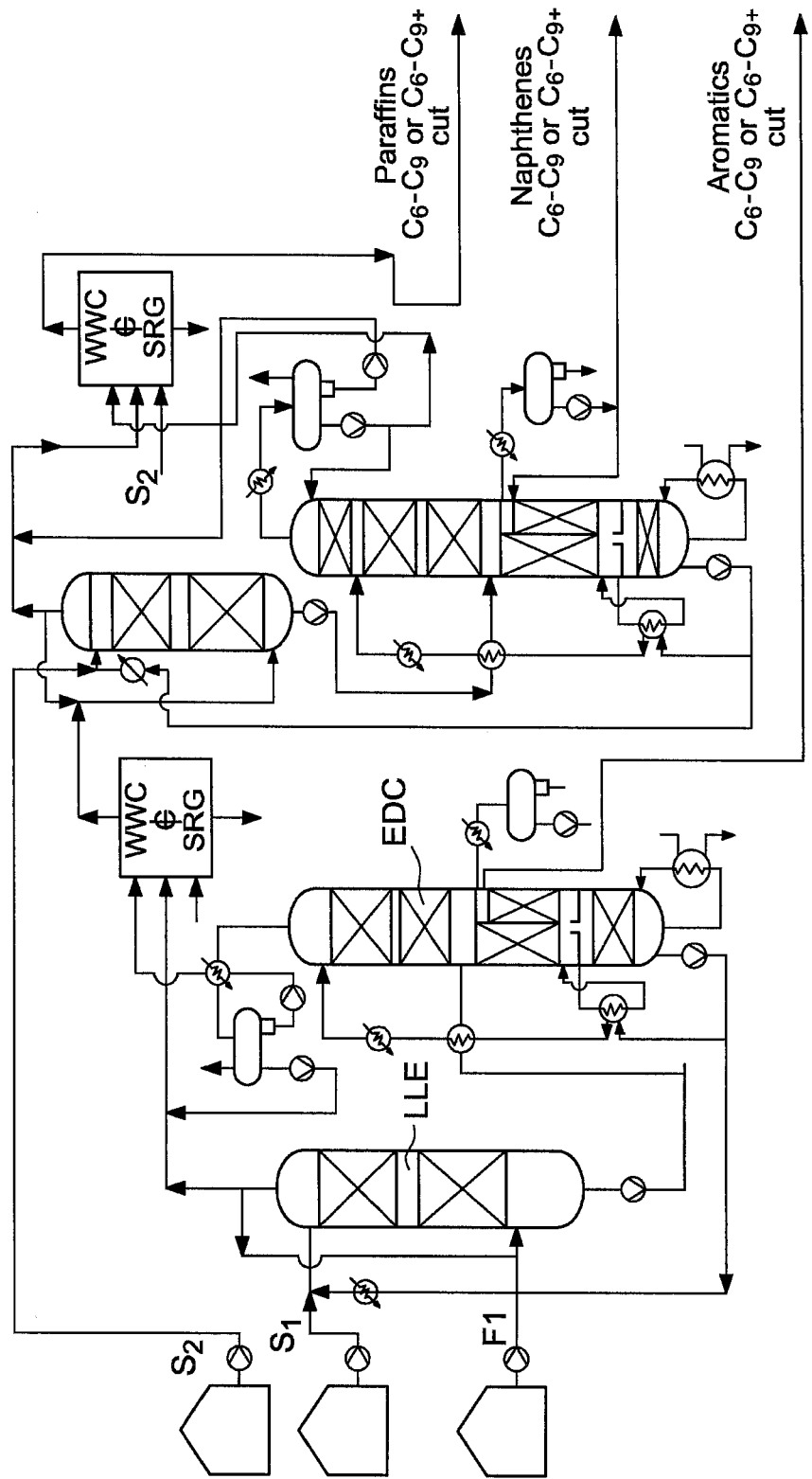
FIG. 8 is a process diagram for the simultaneous production of C6-C9 cut or C6-C9+ cut aromatics, paraffins and naphthenes according to the background art.

In the case of very wide cuts (C6-C9 or C6-C9+), the invention consists in obtaining aromatic, naphthene and paraffin cuts of limited purity. In these cases, the consecutive extractive distillations should be integrated with preventive liquid-liquid extractions (FIG. 8).

The invention is not of practical interest only for charges with a very large content of aromatics (>90%), such as coke oven light oil: in this case, in fact, the second half of the partitioned column might be affected only by a very small stream of non-aromatics.

In a perspective of economically interesting use of said second half of the column in the case cited above, said second half of the column would have to be affected also by a charge of other origin (non-aromatics from reformate or other feedstocks).

For the obtainment of mixes of naphthenes or individual naphthenes with high purity, said cuts may contain only small quantities of olefins. The excess olefin quantities, therefore, must have been or must be removed with convenient hydrogenation/alkylation processes or others.

The method is particularly useful when one wishes to obtain, in addition to aromatic hydrocarbons (B or BT, or aromatic BTX), cyclohexane and/or methylcyclopentane and/or cyclopentane or n-hexane (pure or for technical use) and/or n-heptane (pure or for technical use).

In one embodiment, shown in FIG. 11, the method according to the present invention for separating and recovering C6-C7 aromatics (benzene-toluene) or C6-C8 aromatics (benzene-toluene-xylenes) with high purity and C6-C7 or C6-C8 naphthene cuts and, separately, C6-C7 or C6-C8 paraffin cuts from a crude mix of C6-C7 or C6-C8 hydrocarbons, comprises the steps of:

1. Providing a column, i.e., a vertical elongated container, provided with an internal partition, the container and the partition forming first and second longitudinal chambers inside the elongated container;

2. Preparing inside each longitudinal chamber a partition wall that is provided only on one side with a roof for isolation against the overlying chamber part, creating first and second longitudinal subchambers;

3. Feeding the crude mix into the first longitudinal chamber kept in a first preset range of operating temperatures and at a first preset operating pressure;

4. Feeding a mix of extraction solvents into the first longitudinal chamber in a region that lies above the feed of the crude mix: said solvent mix can contain water as a co-solvent and, as primary solvents, sulfolane, N-methyl-pyrrolidone, N-formylmorpholine, tetraethyleneglycol;

5. Feeding to the head for the first longitudinal chamber a liquid reflux having a selected composition, essentially without aromatic hydrocarbons; said reflux can be constituted by a predominantly aqueous or predominantly hydrocarbon phase;

6. In the preferred embodiment (FIGS. 9A/B), the reflux into the head of the first longitudinal chamber is constituted by an aqueous phase that originates from the separator of the condensate of the head extraction from the second longitudinal chamber;

7. In another embodiment (FIGS. 9A/B), said reflux is constituted by paraffin hydrocarbons that originate from the same condensate separator as the head extraction of the second longitudinal chamber;

8. In another embodiment (FIGS. 9A/B) said reflux is constituted by a combination of part of the paraffin hydrocarbons produced at the head by the second longitudinal chamber and of the naphthene extract of the second longitudinal subchamber;

9. Extraction from the head of the first longitudinal chamber of a first fraction of head vapors, which comprises essentially non-aromatic hydrocarbons and optionally water, which, through an internal channel provided between the two longitudinal chambers, fully feeds the second longitudinal chamber without dissipating the condensation heat of said vapors (FIGS. 9A/B).

10. In an alternative embodiment, not shown, a part of a first fraction of head vapors, which essentially comprises non-aromatic hydrocarbons and optionally water, feeds through an internal channel provided between the two longitudinal chambers, the second longitudinal chamber while the remaining part can optionally constitute a non-aromatic product after separation from any water and/or liquid reflux to said first longitudinal chamber;

11. Extraction of an essentially aromatic distillate in the vapor phase from the first longitudinal subchamber, which is then condensed and partly sent to any further treatments;

12. Feeding an essentially aromatic liquid reflux to the head of the first longitudinal subchamber;

13. Bottom extraction from the first longitudinal chamber of the solvent mix or essentially only of the main solvent if the second solvent is water, essentially without aromatic solute;

14. Second bottom extraction from the first longitudinal chamber of the solvent mix, or of only the main solvent if the second solvent is water, essentially without aromatic solute;

15. Bottom feeding to the first longitudinal chamber of the solvent mix or of the main solvent alone according to the second extraction, conveniently heated/vaporized;

16. Feeding as above said at least one part of the non-aromatic fraction (note: there might be an integration from outside, which is not shown) at the head of the second longitudinal chamber, the second longitudinal chamber being kept in a second preset range of operating temperatures and at a second preset operating pressure;

17. Feeding a mix of extraction solvents into the second longitudinal chamber in a region that lies above the feed of the essentially non-aromatic mix; said solvent mix contains the same components as the solvent mix fed into the first longitudinal chamber, with optional variation of the ratio between main solvent and co-solvent, said co-solvent being possibly water;

18. Feeding to the head of the second longitudinal chamber a reflux having a desired composition, essentially without naphthene hydrocarbons: said reflux can be constituted by a predominantly aqueous or essentially hydrocarbon, paraffin phase;

19. Extraction from the second longitudinal chamber of a second fraction of essentially paraffin head vapors, which is then condensed and partly sent to any further treatments;

20. Extraction of an essentially naphthene distillate in the vapor phase from the second longitudinal subchamber, which is then condensed and partly sent to any further treatments;

21. Feeding an essential naphthene liquid reflux to the head of the second longitudinal subchamber;

22. First extraction from the bottom of the second longitudinal chamber of the solvent mix, or essentially only of the main solvent if the second solvent is water, essentially without naphthene solute;

23. Second extraction from the bottom of the second longitudinal chamber of the solvent mix, or only of the main solvent if the second solvent is water, essentially without naphthene solute;

24. Feeding to the bottom of the second longitudinal chamber of the solvent mix according to the second extraction, conveniently heated/vaporized.

According to another aspect of the invention, which provides for obtaining individual hydrocarbons with high purity, in order to separate C6 aromatics (benzene), cyclohexane and/or methylcyclopentane and/or cyclopentane and/or n-hexane (FIGS. 9A/B, 10A/B/C) from a crude C6 hydrocarbon mix, or having a wider range of carbon atoms, containing the examples in Tables 1, 2, 3, 4, 5, 6, 7, 9), the method comprises, in addition to the steps cited above, the steps of:

25. Feeding the essentially naphthene liquid distillate, at the head of the second longitudinal subchamber, to a fractionation column in which head and/or bottom separation of the cut/naphthene component of greatest interest (e.g., cyclohexane), are to be performed, FIG. 9A;

26. In an alternative embodiment, FIG. 9B, optional feeding of the essentially paraffin liquid condensate from the head of the second longitudinal chamber to a fractionation column in which head and/or bottom separation of the cut/paraffin component of greatest interest (e.g., n-hexane) are to be performed.

The naphthene/paraffin fractionation columns might be plate columns or random filling or structured filling columns but preferably structured filling columns.

In an embodiment which is not shown, the column for post-fractionation of the essentially naphthene or essentially paraffin condensate can have an internal partition for the obtainment, in this case also, of individual naphthene and/or paraffin components with a high degree of purity.

In particular, the operating temperature range of the first longitudinal chamber is comprised between 30° C. and 300° C., preferably between 45° C. and 220° C., and the operating pressure is preferably atmospheric or subatmospheric as a function of the selected solvent or solvent mix, of its tendency to thermal degradation and, if possible, of the heating fluids that are available at the site.

In particular, the extraction from the first longitudinal chamber of a first fraction of head vapors, comprising essentially non-aromatic hydrocarbons, is performed at a temperature comprised between 30° C. and 180° C. for wide cuts (C6-C8), preferably between 45° C. and 100° C. for narrow cuts (C6). Said temperature depends not only on the operating pressure of the chamber but also on the composition of the non-aromatics to be separated (C6 cut with cyclopentane, C6 cut without cyclopentane, C6-C7, C6-C8, etc.) reaching the maximum temperatures when a C6-C8 cut is involved.

In particular, the essentially aromatic head fraction of the first longitudinal subchamber is extracted at a temperature comprised between 70° C. and 160° C., preferably between 80° C. and 110° C. in the presence of C6 narrow cuts.

In particular, the concentration of C6 or C6-C7 or C6-C8 or C6-C9 or C6-C9+ aromatics in the crude mix (prior to fractionation) is comprised between 2% and 90% by volume and preferably between 10% and 85% by volume. This concentration can vary considerably as a function of the nature (NGL/naphtha/reformate/pyrolysis gasoline) and of the crude of origin of the charge, of the process to which it has been subjected beforehand and of the conditions of severity in which it has been performed. Likewise, the concentrations in the same ranges of carbon atoms of paraffins and naphthenes can vary.

In particular, the operating temperature range of the second longitudinal chamber is comprised between 30° C. and 300° C., preferably between 45° C. and 220° C., and the operating pressure of the second longitudinal chamber is probably atmospheric or subatmospheric as a function of the preselected solvent or solvent mix, of its tendency to thermal degradation and if possible of the heating fluids available on site.

In particular, the essentially paraffin head fraction is extracted from the second longitudinal chamber at a temperature comprised between 30° C. and 180° C. in the presence of C6-C8 wide cuts, preferably between 40° C. and 100° C. in the presence of C6 narrow cuts. Said temperature depends not only on the operating pressure of the chamber, but also on the composition of the paraffins to be separated (C6 cut with the presence of C5, C6-C7 cut, C6-C8 cut), reaching the maximum temperatures when a C6-C8 cut is involved.

In particular, the essentially naphthene head fraction of the second longitudinal subchamber is extracted at a temperature comprised between 40° C. and 160° C. in the presence of C6-C8 wide cuts, preferably between 45° C. and 110° C. in the presence of C6 narrow cuts.

The method provides for the use of solvent mixes both in the first longitudinal chamber and in the second longitudinal chamber, and said solvent mixes can in particular be constituted by

- sulfolane or N-methylpyrrolidone or N-formylmorpholine or tetraethylene glycol as a primary solvent of the first longitudinal chamber in a fraction comprised between 99.9% and 80%, preferably between 99.9% and 90%: as a primary solvent mixes of said solvents with water, which becomes the third solvent, can also be used (see Patents and referenced literature);
- water as a secondary solvent of the first longitudinal chamber in a fraction comprised between 0.1% and 20%, preferably between 0.1% and 10%;
- sulfolane or N-methyl pyrrolidone or N-formylmorpholine or tetraethylene glycol as a primary solvent of the second longitudinal chamber in a fraction comprised between 99.9% and 80%, preferably between 99.9% and 90%;
- water as a secondary solvent of the second longitudinal chamber in a fraction comprised between 0.1% and 20%, preferably between 0.1% and 10%.

The use of the same primary and secondary solvent (water) for the extractive distillation operations makes it possible to halve the number of storage units assigned thereto and to manage in an integrated manner in particular the recycling of water and of the solvent, as a person skilled in the art can understand clearly.

The use of the same primary solvent and the adjacent arrangement of the two longitudinal chambers, moreover, facilitate thermal integration, making it constructively easier to recover any excess heat that is available on the stream of the solvent to the second extractive distillation chamber on the streams to which it is necessary to transfer heat on the side of the first extraction chamber or vice versa and/or to any fractionation columns arranged upstream, downstream or in the stream between the two extractive distillation columns. The provision of said recoveries can be facilitated by means of the optimization of the pressure/temperature variables and the primary solvent/secondary solvent ratio used for the two extractive distillation chambers, which must be selected in each instance as a function of the charge mixes and of the desired products.

If, in addition to n-hexane and other paraffin hydrocarbons with six carbon atoms, C6 aromatics (benzene) and C6 naphthenes (MCP and cyclohexane) and optionally C5 (cyclopentane), the available mix contains hydrocarbons with a greater or smaller number of carbon atoms, said mix must be pre-fractionated beforehand with a known method, which is not described in detail herein.

A further advantage is furthermore provided by the possibility of regenerating solvent drawn from the bottom of the second longitudinal chamber and feed it, regenerated, to the first longitudinal chamber.

The opposite is also possible but is not recommended if the content of residual aromatics specified for the naphthenes to be produced must be very low (<100 ppm).

FIG. 9A/9B schematically illustrates processes according to the invention for obtaining pure benzene and cyclohexane (9A) as main products; C6 paraffins (or also nC6 depending on the charge used and on how the first pre-fractioning occurs in the section 100) and a stream rich in methylcyclopentane as byproducts and (9B) pure benzene and normal-hexane as main products; C6 naphthenes and a stream rich in isohexanes (with a high octane number) as byproducts, using the column divided internally and longitudinally into two right and left chambers for performing the consecutive extractive distillations.

The process unit can include:

1. A section 100 for pre-fractioning the charge, provided according to the background art and fed, by way of non-limiting example, with hydrocarbon charges such as the ones described in Tables 1-9;

2. A column for consecutive extractive distillations, which comprises the two longitudinal chambers 200 and 300 which include the sections I, II, III, IV and inside each of which chambers there are subchambers for the sections IIIs and IIId for recovery of aromatics and naphthenes respectively;

3. Auxiliary devices for the column are, in addition to the interiors of the various sections constituted by fractionation plates or preferably by structured fillings, dispensers of liquid/vapors, flue plates for separation of the sections III and IV respectively, pumps for recycling the regenerated solvent mix at the bottom of the chambers 200 and 300 (P4 and P 40), bottom reboilers E6 and E16, lateral reboilers E5 and E15 for recovery of aromatics and naphthenes, preheaters of the charge/charges (E3 in the example), final coolants of the solvents E2 and E12 adapted to control the temperature for feeding solvents to the extractive distillation chambers (between the section I and the section II), condensers of the vapors of recovered aromatics and naphthenes E4 and E14, receivers/separators V2 and V4 of said hydrocarbons recovered from the entrained stripping water co-solvent, pumps P3 and P30 for transferring aromatics/naphthenes to storage/reflux, pumps for recovering/ recycling water co-solvent from said separators (not shown in the figure), a condenser of the paraffin vapors E11 of the head of the chamber 300, a receiver/separator V3 of the paraffin condensate and of the water entrainments, pumps P10 for reflux/sending to recovery the washing water/reflux of the paraffin hydrocarbons at the head of the chamber 300, pumps P20 for sending the paraffin hydrocarbons to reflux chamber 200; the pumps P30 send the naphthene intermediate recovered from the extractive distillation chamber 300 to the fractionation column 400$f$.

In the case of the diagram according to FIG. 9A, naphthene fractionation column 400$f$; said column, provided with interiors (plates or fillers), is also provided with a condenser E50 of the head vapors, a condensate receiver V50, pumps P50 for reflux/sending to storage the light naphthene cut rich in methylcyclopentane, a column bottom reboiler E51 fed with low condensing pressure steam having an adequate thermal level or, as an alternative, with waste streams of solvent regenerated from the bottom of the chambers 200 and/or 300 depending on the thermal balance of the various process units/sections, pumps P52 for sending to storage the pure cyclohexane obtained at the bottom of the column 400.

In the case of the diagram of FIG. 9B, paraffin fractionation column 400$f$; said column, provided with interiors (plates or fillers), is also provided with a condenser E50 of the head vapors, a condensate receiver V50, pumps P50 for reflux/sending to storage the C6 iso-paraffins, column bottom pumps 400, P52 for sending to storage the pure normal hexane produced, column bottom reboiler E51 powered with low condensing pressure steam having an adequate thermal level or, as an alternative, with waste streams of solvent regenerated from the bottom of the chambers 200 and/or 300 depending on the thermal balance of the various process units/sections.

In detail:

the hydrocarbon charge F1, which originates from dedicated storage, is fed to the pre-fractioning section 100, where the C6 light fractions and the lighter unwanted fractions and the unwanted C7 heavy fractions and heavier are removed with a known method. In the case of FIG. 9B, the distillation range of the product F2 of this section is centered on a C6 cut with such a distillation interval as to exclude the presence of paraffins with a boiling point higher than that of n-hexane.

Said pre-fractioning section 100 can be part or not of the same industrial complex in which the consecutive extractive distillation unit is installed or is intended to be installed. If said section is installed elsewhere, the hydrocarbon cut of interest obtained from it would have to be stored in an adapted storage and fed (F2) to the consecutive extractive distillation column. If the section is installed in the industrial complex according to the consecutive extractive distillation column, this last column might be fed by the cut produced by it (F2), as well as by a cut that originates externally to the site (F3).

The pretreated hydrocarbon charge (F2+F3) is preheated in the heat exchangers E3 by means of recovered heat made available by the regenerated solvent mix from the chamber bottom 200 of the consecutive extractive distillation column (CDEC). Said charge is then fed to the chamber 200 of the CDEC in a region which is intermediate between the regions II and III of said chamber.

In the chamber 200, the left chamber of the CDEC, the separations between aromatics and non-aromatics are performed with the aid of the mix of solvents used.

Respectively:

section I has the purpose of recovering traces of the (primary) solvent from the non-aromatics;

section II is the section for rectification, in which the non-aromatics are cleaned, with the aid of the solvent mix, from the aromatics;

the section III or III principal (IIIp) is the stripping section, in which in particular the aromatics are cleaned from the presence of non-aromatics in the mix with the solvents;

the subsection IIIs is the lateral rectification for removal of the solvent (primary solvent) from the recovered aromatics;

the section IV is the solvent stripping section, in which the solvent is cleaned from the presence of aromatics before it is recycled.

The section III is divided from the subsection Ms (left) by means of a wall which forms two separate areas, in which, as is known, the incoming vapors have the same composition and their content of non-aromatics must match the quality required for pure aromatics.

The head vapors of the chamber 200, constituted by non-aromatics which are practically free from aromatics, are fed by an appropriate distribution unit, through an adapted channel provided in the longitudinal wall (optionally a double wall) for separation between the chambers 200 and 300, to the chamber 300 in a region which is intermediate between the sections II and III of said longitudinal chamber 300.

At the head of the column, above the section I, there is also an opening for introducing, with an appropriate liquid dispenser, the preferably aqueous or partially aqueous reflux, partially constituted by non-aromatics of external origin (F5) and/or by paraffin hydrocarbons of the head of the chamber 300 and/or by naphthene hydrocarbons of the head of the subsection IIId (right).

Moreover, the chamber 200 receives the solvent mix MS1 in the region comprised between the sections I and II, through an adapted inlet opening, with an appropriate distribution unit for the liquid solvent mix. The solvent mix can be constituted by a primary solvent, sulfolane or N-methyl pyrrolidone or N-formylmorpholine or tetraethylene glycol (primary solvent of the longitudinal chamber 200) in a fraction comprised between 99.9% and 80%, preferably between 99.9% and 90%, and by water as a secondary solvent of the first longitudinal chamber in a fraction comprised between 0.1% and 20%, preferably between 0.1% and 10%: as a primary solvent, as an alternative, it is also possible to use mixes of said solvents with water, which becomes the third solvent.

Typically, the extractive distillation chamber 200 can include any number of equivalent plates; by way of example, it can have a number of equivalent plates equal to 100; the section I might have a number of equivalent plates equal to 20 (so as to limit the parts per million of aromatics that are present in the non-aromatics and therefore in the cyclohexane).

Moreover, it is necessary to limit the content of aromatics that enter with the reflux 6 (if possible below 50 ppm).

The section II, for example, can have 15 equivalent plates.

The ratio MS1/(F2+F3), solvent mix/charge mix can vary between 1:1 and 20:1 depending on the preselected solvent mix, on the operating conditions of the chamber and on the composition of the charge mix.

The section III and the subsection IIIs, by way of example, can have 40 equivalent plates.

The section III and the section IV are separated by a flue plate which must ensure the necessary head of liquid for circulation to the lateral reboiler E5.

The section IV, by way of example, can have 25 equivalent plates.

The aromatic vapors are extracted through an opening provided in the top of the subchamber IIIs, condensed in the condensers E4, and then reach the separator V2 provided with a sump for the separation of aromatic hydrocarbons and secondary solvent (water).

The aromatic hydrocarbons separated from the water in the separator cited above are drawn by the pumps P3 and partly sent to reflux above the last plate of the section IIIs through an adapted opening in the chamber 200 and an appropriate distribution unit and partly sent to storage, constituting the required aromatic product.

The water separated in the sump of the separator V2 is recovered by means of pumps, not shown in the figure, and returned to circulation.

Rich solvent is drawn from the flue plate PCs of the chamber 200 and the aromatic fractions stripped in section III must be recovered from it. For this purpose, said solvent, by means an appropriate opening and a pipe, feeds the lateral reboiler E5, which is fed with hot regenerated solvent; the partially vaporized rich solvent returns to the column with an adapted opening and a vapor-liquid distribution unit arranged in an area above the flue plate PCs cited above.

From the bottom of the chamber 200 a first opening is formed for drawing the solvent that is practically free from aromatic hydrocarbons by means of an adopted pipe and pumps P4, to be recycled at the head of the section II after appropriate recovering of heat and thermal conditioning; the solvent to be recirculated to the bottom reboiler E6 is drawn from a second opening and the heat complement required for extractive distillation is supplied to it therein: said reboiler can be supplied with high-pressure steam or with another source of adequate thermal level (hot oil, reboiler oven, . . . ).

The non-aromatic vapors of the charge at the chamber 300, as cited above, are fed to said chamber by means of an adapted channel and distribution unit provided within the partition (optionally a double partition) that divides the chambers 200 and 300 and respectively between the section II and III of the chamber 300.

As already mentioned, any non-aromatic charge that originates from storage might be fed by means of a line 6 to the head of the section I of the chamber 200.

In the chamber 300, the right one of the CDEC, the separations between naphthenes and paraffins are performed with the aid of the mix of solvents used.

Respectively:
the section I has the purpose of recovering traces of the (primary) solvent from the paraffins;
the section II is the rectification section in which the paraffins are cleaned, with the aid of the solvent mix, from the naphthenes;
the section III is the stripping section, in which in particular the naphthenes are cleaned from the presence of paraffins in the mix with the solvents;
the subsection IIId is the lateral rectification for removal of the solvent (primary solvent) from the recovered naphthenes;
the section IV is the solvent stripping section, in which the solvent is cleaned from the presence of naphthenes before it is recycled.

The section III is divided from the subsection 3d (right) by means of a wall that forms two separate areas, in which, as is known, the incoming vapors have the same composition and their paraffin content must comply with the quality required for pure naphthenes (cyclohexane).

The head vapors of the chamber 300, constituted by paraffins that are practically free from naphthenes, are sent by means of an appropriate opening and a pipe to the condensers E11 and from there to the receiver V3 with an adapted sump for separating the entrained water from the paraffins: from there, the aqueous phase separated in the sump is collected by means of the pumps 10 and sent at least partly as reflux through an appropriate pipe, an opening and a corresponding distribution unit, to the head of the chamber 300. A second part of the aqueous phase is instead sent to recovery. The paraffin hydrocarbon phase, collected by the pumps P20, is sent, in the process alternative 9A, to storage, in the process case 9B to the fractionation column 400f or partially to act as reflux at the chamber 200.

Furthermore, the chamber 300 receives the solvent mix MS2 in a region comprised between the sections I and II, through an adapted insertion inlet, with an adapted distributor for the liquid solvent mix. The solvent mix can be constituted by a primary solvent, sulfolane or N-methyl pyrrolidone or N-formylmorpholine or tetraethylene glycol (primary solvent of the longitudinal chamber 200) in a fraction comprised between 99.9% and 80%, preferably between 99.9% and 90%, and water as a secondary solvent of the first longitudinal chamber in a fraction comprised between 0.1% and 20%, preferably between 0.1% and 10%: as a primary solvent it is also possible, as an alternative, to use mixes of said solvents with water, which becomes the third solvent.

Typically, the extractive distillation chamber 300 can include any number of equivalent plates; by way of example, it can have a number of equivalent plates equal to 100; the section I might have a number of equivalent plates equal to 20 (in the case of the process according to FIG. 9A, it might not be justified economically to limit the ppm of naphthene that are present in the paraffins and therefore said number of plates might depend exclusively on the extent of the losses of primary solvent, whereas in the case of the process according to FIG. 9B, depending on whether one wishes to obtain an n-hexane with high purity or not, it might be economically justified to limit the ppm of naphthenes that are present in the paraffins).

The section II, by way of example, can have 15 equivalent plates.

The ratio MS2 (solvent mix)/charge mix from the head of the chamber 200 can vary between 1:1 and 20:1, depending on the preselected mix of solvents, on the operating conditions of the chamber 300 and on the composition of the charge mix of said chamber.

The section III and the subsection IIId, by way of example, can have 40 equivalent plates (in this case, since the difference of affinity for paraffin and naphthene solvents is less pronounced than the difference between non-aromatics and aromatics, the number of plates required for a good stripping of the paraffins might be higher).

The sections III and IV are separated by a flue plate, which must ensure the necessary head of liquid for circulation to the lateral reboiler E15.

The section IV can have, by way of example, 25 equivalent plates.

The naphthene vapors are extracted through an opening provided on the top of the subchamber IIId, condensed in the condensers E14, and then reach the separator V4, provided with a sump for separation of naphthene hydrocarbons and secondary solvent (water).

The naphthene hydrocarbons, rich in methylcyclopentane, separated from the water in the separator cited above, are collected by the pumps P30 and partly sent to reflux over the last plate of the section IIId through an appropriate opening in the chamber 300 and an appropriate distribution unit and partly, in the case of the process according to FIG. 9A, to the fractionation column 400f for the separation of pure cyclohexane from the lighter naphthenes (stream rich in methylcyclopentane), whereas in the case of the process according to FIG. 9B, to dedicated storage.

The water separated in the sump of the separator V4 is recovered by means of pumps, not shown in the figure, and returned to circulation.

From the flue plate PCd of the chamber 300, rich solvent is drawn from which it is necessary to recover the naphthene fractions stripped in section III. For this purpose, said solvent, by means of an adapted opening and pipe, supplies the lateral reboiler E15, which is fed with hot regenerated solvent; the partially vaporized rich solvent returns to the column by means of an adapted opening and a vapor-liquid distribution unit arranged in an area above the flue plate PCd cited above.

From the bottom of the chamber 300 a first opening is formed for drawing the solvent that is practically free from naphthene hydrocarbons by means of an adapted pipe and pumps P40, to be recycled at the head of the section II after adapted heat recoveries and thermal conditioning; the solvent to be recirculated to the bottom reboiler E16 is drawn from a second opening, and the heat complement required for extractive distillation is supplied therein: said reboiler can be supplied with steam at high pressure or with another source of adequate thermal level (hot oil, re-boiler oven, . . . ).

In the case of the process according to FIG. 9A, the naphthene fraction produced by the chamber 300 subsection IIId is supplied by means of pumps P30 and a line 53 to the column 400f.

Said column provides, by means of known methods, the separation of the pure bottom cyclohexane from the lighter naphthenes (stream rich in methylcyclopentane with the optional presence, in addition to cyclohexane, of cyclopentane).

The heat for reboiling said column might be provided at least partly by the bottom solvents of the chambers 200/300.

The pure column bottom cyclohexane is sent to storage by means of the pumps P52.

The head vapors of the column 400, condensed in the condensers E50, collect in the receiver V50: from there the condensed liquid, by means of pumps P50, is partly refluxed to the column 400 and partly sent to storage.

In the case of the process according to FIG. 9B, the net paraffin fraction that is produced at the head of the chamber 300 and is collected in the receiver V3 is supplied to the column 400f by means of pumps P20 and lines 45/45'.

Said column provides, by virtue of known methods, the separation of the solvent quality normal hexane (for various industrial or food uses), from the bottom, from the lighter paraffins (essentially iso-C6).

The heat for reboiling said column is provided by the reboiler E51, which is fed with steam at low condensing pressure of adequate thermal level: part of said heat might be provided by the bottom solvents of the chambers 200/300.

The normal hexane of desired quality, from the bottom of the column, is sent to storage by means of the pumps P52.

The head vapors of the column 400 (essentially isohexanes), condensed in the condensers E50, collect in the receiver V50: from there, the condensed liquid, by means of pumps P50, is partly refluxed to the column 400 and partly sent to storage.

FIGS. 10A/B and C illustrate variations to the processes according to the preceding FIGS. 9A and 9B, in which the column for consecutive extractive distillations has two entirely separate chambers 200 and 400 which are not mutually connected. The rectification, in the column 300 of the non-aromatic intermediate obtained after the first extractive distillation to obtain the desired pure naphthene products (cyclohexane or methylcyclopentane or cyclopentane) or pure paraffin products (n-hexane) is performed before performing the second extractive distillation.

The disadvantage of this process is that it is necessary to provide an onerous system for condensation, accumulation, reflux and transfer-feeding to the column 300, which were not necessary in the alternatives 9A and 9B. In this case, however, it is possible to reduce the dimensions of the chamber 400, because the unwanted non-aromatic byproducts are at least partly removed by distillation.

The alternative 10C illustrates the possibility of making the section 300 and 400 run by campaigns, achieving alternatively the production of pure cyclohexane or pure methylcyclopentane while the chamber 200 continues to produce benzene and non-aromatics, which can be fed to the section 300 or can be stored in the tank of the non-aromatics to be taken subsequently as feedstock F5.

The process alternative according to FIG. 11 shows schematically a process according to the invention for obtaining BT or BTX (or TX, XC9 or TXC9) aromatic mixes with a small distillation range and simultaneously the corresponding pure naphthene mixes (NC6-NC7, NC6-NC7-NC8 or NC7-NC8, NC8-NC9 or NC7-NC8-NC9) and normal paraffin mixes (P6-P7, P6-P7-P8 or P7-P8, P8-P9 or P7-P8-P9), using the column divided internally and longitudinally into two right and left chambers to perform the consecutive extractive distillations.

In this case, the process unit does not provide for the steps of pre-fractioning and/or post-fractioning (sections 100 and 400f) but includes the other components of the solutions 9A/9B for the consecutive extractive distillation column (CDEC), the description of which we omit.

In this case, the pumps P30 send the recovered naphthenes from the extractive distillation chamber 300 to dedicated storage.

In detail, for process diagrams that provide for the use of the channel for connection between one chamber and the other of the consecutive extractive distillation column (CDEC).

The hydrocarbon charge F1, which arrives from dedicated storage, is preheated in the exchangers E3 by means of recovery heat that is made available by the regenerated solvent mix from the bottom of the chamber 200 of the consecutive extractive distillation column (CDEC). Said charge is then fed to the chamber 200 of the CDEC in a region that is intermediate between the regions II and III of said chamber.

In the left chamber 200 of the CDEC, separations between aromatics and non-aromatics occur with the aid of the solvent mix used.

Respectively:

the section I is meant to recover traces of the (primary) solvent from the non-aromatics;

the section II is the rectification section in which the non-aromatics are cleaned, with the aid of the solvent mix, from the aromatics;

section III is the stripping section, in which in particular the aromatics are cleaned from the presence of non-aromatics in the mix with the solvents;

the subsection IIIs is the lateral rectification for removal of the solvent (primary solvent) from the recovered aromatics;

the section IV is the section for stripping the solvent, in which the solvent is cleaned from the presence of aromatics before being recycled.

The section III is divided from the subsection Ms (left) by means of a wall that forms two separate areas, in which, as is known, the incoming vapors have the same composition and their content of non-aromatics must comply with the quality required for pure aromatics.

The head vapors of the chamber 200, constituted by non-aromatics that are practically free from aromatics, are fed with an adapted distribution unit, by means of an adapted channel provided in the longitudinal wall (optionally double wall) that separates the chambers 200 and 300, to the chamber 300 in a region that is intermediate between the sections II and III of said longitudinal chamber 300.

At the head of the column, above the section I, there is also an opening for introducing, with an appropriate liquid distribution unit, the reflux, which is preferably aqueous or partially aqueous and partially constituted by non-aromatics of external origin (F2) and/or is constituted by paraffin hydrocarbons from the head of the chamber 300 and/or naphthene hydrocarbons from the head of the subchamber IIId.

Moreover, the chamber 200 receives the solvent mix MS1 in a region comprised between the sections I and II, through an adapted inlet, with an adapted distribution unit for the liquid solvent mix. The solvent mix can be constituted by a primary solvent, sulfolane or N-methyl pyrrolidone or N-formylmorpholine or tetraethylene glycol (primary solvent of the longitudinal chamber 200) in a fraction comprised between 99.9% and 80%, preferably between 99.9% and 90%, and water as a secondary solvent of the first longitudinal chamber in a fraction comprised between 0.1% and 20%, preferably between 0.1% and 10%: as a primary solvent it is also possible to use, as an alternative, mixes of said solvents with water, which becomes the third solvent.

Typically, the extractive distillation chamber 200 can include any number of equivalent plates; by way of example, it can have a number of equivalent plates equal to 100; the section I might have a number of equivalent plates equal to 20 (depending on the need to limit or not the ppm of aromatics that are present in the non-aromatics).

Moreover, it can be necessary to limit the content of aromatics that enter with the reflux 6 (for example below 50 ppm).

The section II can, by way of example, provide for 15 equivalent plates.

The ratio MS1/(F1), solvent mix/charge mix, can vary between 1:1 and 20:1 depending on the selected solvent mix, on the operating conditions of the chamber and on the composition of the charge mix.

The section III and the subsection IIIs, by way of example, can provide for 40 equivalent plates.

The section III and the section IV are separated by a flue plate, which must ensure the necessary head of liquid for circulation to the lateral reboiler E5.

The section IV can, by way of example, provide for 25 equivalent plates.

The aromatics vapors are extracted through an opening provided in the top of the subchamber IIIs, condensed in the condensers E4, and then reach the separator V2 provided with a sump for the separation of aromatic hydrocarbons and secondary solvent (water).

The aromatic hydrocarbons separated from the water in the above cited separator are drawn by the pumps P3 and partly sent to reflux over the last plate of the section IIIs by means of an adapted opening in the chamber 200 and an adapted distribution unit and partly sent to storage, forming the required aromatic product.

The water separated in the sump of the separator V2 is recovered by means of pumps, not shown in the figure, and returned to circulation.

Rich solvent is drawn from the flue plate PCs of the chamber 200 and the aromatic fractions stripped in section III must be recovered from it. For this purpose, said solvent, through an adapted opening and a pipe, is fed into the lateral reboiler E5, which is fed with hot regenerated solvent; the partially vaporized rich solvent returns into the column through an appropriate opening and a vapor-liquid distribution unit arranged in an area above the flue plate PCs cited above.

From the bottom of the chamber 200 a first opening is formed for drawing the solvent that is practically free from aromatic hydrocarbons by means of an adapted pipe and pumps P4, to be recycled at the head of the section II after adapted heat recoveries and thermal conditioning; the solvent to be recirculated to the bottom boiler E6 is drawn from a second opening, and the heat complement required for extractive distillation is provided therein: said reboiler can be supplied with steam at high pressure or with another source of adequate thermal level (hot oil, reboiler oven, . . . ).

The non-aromatic vapors that charge the chamber 300, as cited above, are fed to said chamber by means of an adapted channel and distribution unit provided within the partition (optionally a double partition) that divides the chambers 200 and 300 and respectively between the section II and III of the chamber 300.

As already mentioned, any non-aromatic charge that arrives from storage might be fed by means of a line 6 to the head of the section I of the chamber 200.

In the chamber 300, the right chamber of the CDEC, the separations between naphthenes and paraffins are performed by means of the solvent mix that is used.

Respectively:

the section I has the purpose of recovering traces of the (primary) solvent from the paraffins;

the section II is the rectification section, in which the paraffins are cleaned, with the aid of the solvent mix, from the naphthenes;

the section III is the stripping section, in which in particular the naphthenes are cleaned from the presence of paraffins in the mix with the solvents;

the subsection IIId is the lateral rectification for removal of the solvent (primary solvent) from the recovered naphthenes;

the section IV is the section for stripping the solvent, in which the solvent is cleaned from the presence of naphthenes before being recycled.

The section III is divided from the subsection IIId (right) by means of a wall that forms two separate areas in which, as is known, the incoming vapors have the same composition and their paraffin content must comply with the quality required for pure naphthenes.

The head vapors of the chamber 300, constituted by paraffins practically free from naphthenes, are sent by means of an adapted opening and pipe to the condensers E11 and from there to the receiver V3 with an adapted sump for separating the entrained water from the paraffins; from there, the aqueous phase separated in the sump is collected by means of the pumps P10 and sent at least partly as reflux through an adapted pipe, opening and corresponding distribution unit to the head of the chamber 300. A second part of the aqueous phase is instead sent to be recovered. The paraffin hydrocarbon phase, collected by the pumps P20, is transferred to dedicated storage and, if required, is partly used to act as reflux to the chamber 200.

The chamber 300 furthermore receives the solvent mix MS2 in a region comprised between the sections I and II, through an adapted inlet, with an adapted distribution unit for the liquid solvent mix. The solvent mix can be constituted by a primary solvent, sulfolane or N-methyl pyrrolidone or N-formylmorpholine or tetraethylene glycol (primary solvent of the longitudinal chamber 200) in a fraction comprised between 99.9% and 80%, preferably between 99.9% and 90%, and water as a secondary solvent of the first longitudinal chamber in a fraction comprised between 0.1% and 20%, preferably between 0.1% and 10%: as a primary solvent it is also possible to use, as an alternative, mixes of said solvents with water, which becomes the third solvent.

Typically, the extractive distillation chamber 300 can include any number of equivalent plates; by way of example, it can have a number of equivalent plates equal to 100; the section I might have a number of equivalent plates equal to 20 (in this case one must assess whether in order to obtain a paraffin mix of high purity it may be economically justified or not to limit the ppm of naphthenes that are present in the paraffins by adding equivalent plates to the section).

The section II can, by way of example, provide for 15 equivalent plates.

The ratio MS2 (solvent mix)/charge mix from the head of the chamber 200 can vary between 1:1 and 20:1, depending on the selected solvent mix, on the operating conditions of the chamber 300 and on the composition of the mix that charges said chamber.

The section III and the subsection IIId, for example, can have 40 equivalent plates (in this case, since the difference of affinity for the paraffins and naphthene solvents is less conspicuous than the difference between non-aromatics and aromatics, the number of plates required for good stripping of the paraffins might be higher).

The sections III and IV are separated by a flue plate which must ensure the necessary head of liquid for circulation to the lateral reboiler E15.

The section IV can, by way of example, provide for 25 equivalent plates.

The naphthene vapors are extracted through an opening provided in the top of the subchamber IIId, condensed in the condensers E14, and then reach the separator V4 provided with a sump for the separation of the naphthene hydrocarbons and the secondary solvent (water).

The naphthene hydrocarbons, separated from water in the separator cited above, are collected by the pumps P30 and partly transferred to reflux over the last plate of the section IIId through an adapted opening in the chamber 300 and an adapted distribution unit and partly transferred to dedicated storage.

The water separated in the sump of the separator V4 is recovered by means of pumps, not shown in the figures, and is returned to circulation.

Rich solvent is drawn from the flue plate PCd of the chamber 300 and the naphthene fractions stripped in section III must be recovered from it. For this purpose, said solvent, through an adapted opening and a pipe, is fed to the lateral reboiler E15, which is supplied with hot regenerated solvent; the partially vaporized rich solvent returns to the column through an adapted opening and vapor-liquid distribution unit arranged in an area above the flue plate PCd cited above.

From the bottom of the chamber 300 a first opening is formed for drawing the solvent that is practically free from naphthene hydrocarbons, by means of an adapted pipe and pumps P40, to the head of the section II to be recycled after adapted heat recoveries and thermal conditioning; the solvent to be recirculated to the bottom reboiler E16 is drawn from a second opening and the heat complement required for extractive distillation is supplied therein: said reboiler can be supplied with high-pressure steam or with another source of adequate thermal level (hot oil, reboiler oven, . . . ).

The methods of the present invention of consecutive extractive distillation can use the same primary solvent.

A surprising effect is obtained by the two consecutive extractive distillations in a single container or column of the present inversion that is divided by an integral wall Top-Down, wherein the two chambers can be operated with chamber bottom temperatures different for the two chambers, with a difference of at least 10-15° C., and by acting on the operative pressures of the two chambers and on the co-solvent water percentage that is normally higher in chamber (300) with respect to chamber (200).

A surprising effect is obtained by the two consecutive extractive distillations in a single container or column of the present inversion that allow a natural fluid circulation for the close location of section IIIp of the chamber 300 and section IIIs of chamber (200).

A surprising effect is obtained by the two consecutive extractive distillations in a single container or column of the present inversion that allow thermally integrating the two chambers; for example, the condensing fluid exiting the subsection IIIs can transfer at least part of the condensation heat to the liquid going down along the sub-section IIIp. The latter would be vaporized by the condensation heat transferred by the condenser E4, and then enter again the same section IIIp, as schematically shown in FIG. 12, but also valid in the columns of the columns of FIGS. 13, 16 and 17. Such a thermal integration, that allows to save heat to be provided with the boiler E16, for example by using High Pressure Steam (HPS), is on the contrary difficult to carry out with two separate columns, the distance between them rendering it prohibitive.

The disclosures in Italian Patent Application No. MI2011A002271 from which this application claims priority are incorporated herein by reference.

The invention claimed is:

1. A column for consecutive extractive distillations, in particular of a crude hydrocarbon mix comprising aromatic, naphthene and paraffin hydrocarbons, comprising a vertical elongated container provided with a head, a bottom and an internal partition that runs vertically from the bottom to the head of said container and divides its internal volume, forming a first longitudinal chamber and a second longitudinal chamber which are adjacent, inside said column, wherein each one of said chambers comprises at least four sections, of which a middle section, a solvent regeneration section arranged below said middle section, a section for separating an affine component which is arranged above said middle section and a section for the recovery of solvent entrained by a less affine fraction arranged above said section for separating an affine component, said middle section being divided into a main section for stripping components that are not affine with the solvent, which is arranged toward the inside of the column and a lateral rectification subsection for removing solvent from the affine components, arranged toward the outside of the column, by means of a vertical partition of the middle section arranged within the middle section, wherein said main section is open at the top and at the bottom and said subsection is open at the bottom and closed at the top so that said main section and said subsection are mutually connected only through an upper region of said solvent stripping or regeneration section, a flue plate being arranged under the middle section; said first chamber having an inlet for the crude hydrocarbon mix arranged between said middle section and said separation section of the first chamber and an inlet for solvents which is arranged between said separation or rectification section for non-aromatics and said solvent recovery section of the first chamber; said second chamber having an inlet for a hydrocarbon mix that comprises naphthene and paraffin hydrocarbons in a region between said middle section and said separation section of the second chamber and a second inlet for solvents which is arranged between said paraffin rectification or separation section and said solvent recovery section of the second chamber; and a channel for connection between the head space of the first chamber and said region between said middle section and said separation section of the second chamber for the inflow of head vapors of the chamber containing naphthene and paraffin hydrocarbons.

2. A method for separating and recovering the components of a crude hydrocarbon mix comprising aromatic, naphthene and paraffin hydrocarbons by consecutive extractive distillations, said method comprising the steps of:
 a) providing a column for consecutive extractive distillations according to claim 1;
 b) feeding said crude hydrocarbon mix into said first chamber through said inlet for the crude hydrocarbon mix, said first chamber being kept within a first preset range of operating temperatures and at a first preset operating pressure;
 c) feeding a first extraction solvent into the first chamber through said first solvent inlet;
 d) extracting from the lateral rectification subsection of said first chamber an essentially aromatic distillate;
 e) sending at least part of the head fraction of the first chamber or a second mix of paraffin and naphthene hydrocarbons obtained by additional separation from at least part of the head vapors of the first chamber, in a region between said middle section and said separation section of the second chamber;
 f) feeding into the second chamber a second extraction solvent through said second solvent inlet;
 g) extracting from the second chamber a head fraction which essentially comprises paraffin hydrocarbons, preferably with a total content of non-paraffins of less than 1% by weight;
 h) extracting from the lateral rectification subsection of said second chamber an essentially naphthene distillate, preferably with a total content of non-naphthenes of less than 1% by weight.

3. The method according to claim 2, wherein said column comprises said internal channel which connects the head space of the first chamber and said region between said middle section and said separation section of the second chamber, forming said inlet for a hydrocarbon mix that comprises naphthene and paraffin hydrocarbons in the second chamber, and wherein in step e) at least part of the head fraction of the first chamber is sent directly to the second chamber by means of said channel.

4. The method according to claim 3, wherein said naphthene distillate of step h) is sent to a fractionation column, where a stream substantially of cyclohexane and a stream rich in methylcyclopentane are separated.

5. The method according to claim 3, wherein said paraffin fraction of step g) is sent to a fractionation column, where a stream rich in n-hexane and a stream rich in iso-hexanes are separated.

6. The method according to claim 2, wherein in step e) at least part of the head fraction of the chamber is sent to a separation column, where a second mix of paraffin and naphthene hydrocarbons is separated.

7. The method according to claim 6, wherein in step e) at least part of the head fraction of the chamber is sent to a rectification column so as to separate said second mix into a head fraction that contains the naphthenes that are lighter than cyclohexane and into a bottom fraction, which essentially comprises C6 normal paraffins and cyclohexane, the bottom fraction being sent to the upper part of the main stripping section of the second chamber through said inlet for hydrocarbon mix comprising naphthene and paraffin hydrocarbons, and wherein a stream substantially of n-hexane, preferably with a purity of >95% by weight, is extracted from the head of the second chamber, and a stream substantially of cyclohexane, preferably with a purity of >99.5% by weight, is extracted from the lateral rectification subsection of said second chamber.

8. The method according to claim 6, wherein in step e) at least part of the head fraction of the chamber is sent to a rectification column so as to separate said second mix into a head fraction that is practically free from cyclohexane and from crude cyclohexane produced as a bottom product, preferably with a purity of 80-95%, said head mix comprising essentially C6 normal paraffins and methylcyclopentane and being sent to the upper part of the main stripping section of the second chamber through said inlet for hydrocarbon mix comprising naphthene and paraffin hydrocarbons, and wherein a stream substantially of n-hexane, preferably with a purity >99.5%, is extracted from the head of the second chamber and a stream substantially of methylcyclopentane, preferably with a purity >99.5%, is extracted from the lateral rectification subsection of said second chamber.

9. A method for separating and recovering the components of a crude hydrocarbon mix comprising aromatic, naphthene and paraffin hydrocarbons, said method comprising the steps of:
 a) providing a column for consecutive extractive distillations according to claim 1;
 b) feeding said crude hydrocarbon mix into the first chamber, said chamber being kept in a first preset range of operating temperatures and at a first preset operating pressure;
 c) feeding a first mix of extraction solvents into the first chamber in a region that lies above the feeding region of said crude mix, wherein said mix of extraction solvents comprises Sulfolane, or N-methyl pyrrolidone, or N-formylmorpholine, or tetraethylene glycol or mixes thereof, and water as a cosolvent;
 d) feeding to the head of the first chamber a liquid reflux mix having a preset composition and comprising water and hydrocarbons, wherein said mix is essentially without aromatic hydrocarbons, said mix can be obtained as a first chamber head product after condensation of extracted vapors and separation of the aqueous phase from the hydrocarbon phase or originate from external storage/purchases/transfers or originate from the head of the second chamber and be essentially aqueous or essentially paraffin or part from the head of the first chamber and part from the head of the lateral rectification subsection of the second chamber of the naphthene phase;

e) extracting from the head of the first chamber a first fraction of head vapors comprising essentially non-aromatic hydrocarbons and water;

f) extracting from the lateral rectification subsection of the first chamber an essentially aromatic distillate in the vapor phase which is condensed and at least partially sent to further treatments, chosen among benzene-toluene-xylene fractionation if the aromatic extract is a BTX mix or to uses of benzene, pro ethylbenzene, cumene, LAB, cyclohexane via hydrogenation, others;

g) feeding to the head of the lateral rectification subsection of the first chamber a liquid reflux mix which comprises essentially aromatic hydrocarbons;

h) extracting from the flue plate that divides the sections IIIp/IIIs from the section IV solvent that is rich in aromatics, recirculating it, preferably with natural circulation, in the reboiler E5, from which, after partial vaporization, it is returned into the chamber below the sections IIIp/IIIs;

i) extracting from the bottom of the first chamber a mix that comprises at least one solvent or essentially only the main solvent if the second solvent is water, wherein the term "essentially" is understood to mean that the residual aromatic content is <0.5%, preferably <0.1%, at least a first part of said mix being sent by natural circulation to a thermosyphon reboiler and thus returns to the bottom of the section IV, and a second part of said mix being sent to pumps for recycling the solvent or solvents, said mix being extracted from the bottom of the first chamber in at least two different extraction lines, or in a single line that is divided into at least two other lines for said first part and said second part of the mix, and then returns to the bottom of the section IV, without aromatic hydrocarbons;

l) feeding to the head of the section II of the first chamber the mix obtained in the last extraction of step h), conveniently cooled by releasing heat into the reboiler, in the preheater of the charge and in the final coolant;

m) sending to the second chamber at least part of the head fraction of step e), after fractionation;

n) feeding into the chamber, at the top of the section II, in a region that lies above the region for feeding the mix to step l), an extraction mix which comprises the same components as the mix in step c), with a variation of the ratio between main solvent and water, if present;

o) feeding to the head of the chamber a liquid reflux mix having a preset composition and comprising water and/or paraffin hydrocarbons, wherein said mix is essentially free from naphthene hydrocarbons, preferably with a content <0.5%, preferably <0.1% of naphthene hydrocarbons, which originates from the head vapors of the second chamber after condensation and separation of the aqueous phase from the paraffin phase, partly recombined in order to constitute the reflux;

p) extracting from the second chamber a fraction of head vapors which comprises essentially paraffin hydrocarbons, which is condensed with the separation of paraffin hydrocarbons and of any water, and sent, at least partially, to further possible treatments, the paraffin fraction being distilled in order to separate N-hexane from iso-hexanes or being separated by adsorption/desorption on 5-angstrom molecular sieves; or used to produce ethylene by S/cracking;

q) extracting from the lateral rectification subsection of the second chamber an essentially naphthene distillate in the vapor phase, which is condensed and at least partially sent to further treatments;

r) feeding to the head of the lateral rectification subsection of the second chamber a liquid mix which comprises essentially naphthene hydrocarbons;

s) extracting from the bottom of the second chamber a mix comprising at least one solvent, or essentially only the main solvent if the second solvent is water, wherein the term "essentially" is understood to mean that the residual naphthene content is <0.5%, preferably <0.1%, at least a first part of said mix being sent by natural circulation to a thermosyphon reboiler and then returning to the bottom of the section IV, and a second part of said mix being sent to pumps for recycling the solvent or solvents, said mix being extracted from the bottom of the second chamber in at least two different extraction lines or in a single line that divides into at least two other lines for said first part and said second part of the mix and then returns to the bottom of the section IV without naphthene hydrocarbons;

t) feeding to the head of the section II of the second chamber the mix obtained in the last extraction of step s), conveniently cooled by transfer of heat in the reboiler, in an external preheater of the charge, which is not shown, and in the final coolant.

10. The method according to claim 9, wherein in step m) the at least one part of the head fraction of step e) is sent to the second chamber by means of said channel which is internal to the column for consecutive extractive distillations which connects the head of the first chamber to the upper part of the main stripping section of the second chamber.

11. The method according to claim 10, wherein said crude hydrocarbon mix is, for example, the one of Table 9 and wherein benzene, cyclohexane and/or methylcyclopentane and/or n-hexane are separated and the liquid distillate of step p) is fed to a fractionation column, in which a naphthene component, preferably cyclohexane, is separated at the head and/or bottom.

12. The method according to claim 10, wherein said crude hydrocarbon mix is, for example, the one given in Table 6, in which benzene, a stream of C6 naphthenes constituted by cyclohexane and/or methylcyclopentane and a stream of C6 paraffins and/or n-hexane are separated and in which the liquid distillate of step o) is fed to a fractionation column in which a paraffin component of commercial purity, preferably n-hexane, is separated at the head and/or bottom.

13. The method according to claim 9 for obtaining benzene and cyclohexane, wherein said crude hydrocarbon mix is, for example, the one of Table 9 and wherein in step m) the at least one part of the head fraction of step e) is sent to a rectification column from which a mix is obtained which comprises predominantly paraffins and cyclohexane and is sent to the second chamber above the main stripping section.

14. The method according to claim 9 for obtaining benzene, an n-hexane-rich stream and methylcyclopentane, wherein said crude hydrocarbon mix is, for example, the one of Table 5 and wherein in step m) the at least one part of the head fraction of step e) is sent to a rectification column from which one obtains at the head a mix that comprises predominantly n-hexane and methylcyclopentane, which is sent to the second chamber above the main stripping section.

15. The method according to one of claim 9, wherein the liquid reflux mix of step d) comprises the aqueous phase that originates from the separation of the condensate of step p) or the paraffin hydrocarbons that originate from the separation of step p) or comprises a part of the paraffin hydrocarbons that originate from the separation of the condensate of step p) and at least one part of the naphthene mix of step o).

16. The method according to claim 2, wherein in the first chamber the operating temperature is comprised between 30° C. and 300° C., preferably between 45° C. and 220° C., and the operating pressure is preferably atmospheric or subatmospheric.

17. The method according to claim 2, wherein in the second chamber (300) the operating temperature is comprised between 30° C. and 300° C., preferably between 45° C. and 220° C., and the operating pressure is preferably atmospheric or subatmospheric.

18. The method according to claim 2, wherein said first solvent or/and said second solvent comprises Sulfolane or N-methyl pyrrolidone or N-formylmorpholine or tetraethylene glycol or a mix thereof in a percentage comprised between 99.9% and 80%, preferably between 99.9% and 90%, and water in a percentage comprised between 0.11% and 20%, preferably between 0.1% and 10%.

19. The method according to claim 2, furthermore comprising a step of pre-fractionation of the crude hydrocarbon mix prior to step b) for the separation of C5 and lighter hydrocarbon fractions or hydrocarbons with a lower boiling point than n-hexane and/or fractions with a number of carbon atoms or a boiling point that are higher than that of hydrocarbons or of the mixes of interest, for example C7 hydrocarbons and higher ones or having a higher boiling point than cyclohexane in order to obtain paraffin and/or naphthene mixes and/or individual paraffin hydrocarbons (N-hexane) and/or naphthene hydrocarbons (methylcyclopentane, cyclohexane) of commercial purity.

20. The method according to claim 9, wherein in the first chamber the operating temperature is comprised between 30° C. and 300° C., preferably between 45° C. and 220° C., and the operating pressure is preferably atmospheric or subatmospheric.

21. The method according to claim 9, wherein in the second chamber (300) the operating temperature is comprised between 30° C. and 300° C., preferably between 45° C. and 220° C., and the operating pressure is preferably atmospheric or subatmospheric.

22. The method according to claim 9, wherein said first solvent or/and said second solvent comprises Sulfolane or N-methyl pyrrolidone or N-formylmorpholine or tetraethylene glycol or a mix thereof in a percentage comprised between 99.9% and 80%, preferably between 99.9% and 90%, and water in a percentage comprised between 0.11% and 20%, preferably between 0.1% and 10%.

23. The method according to claim 9, furthermore comprising a step of pre-fractionation of the crude hydrocarbon mix prior to step b) for the separation of C5 and lighter hydrocarbon fractions or hydrocarbons with a lower boiling point than n-hexane and/or fractions with a number of carbon atoms or a boiling point that are higher than that of hydrocarbons or of the mixes of interest, for example C7 hydrocarbons and higher ones or having a higher boiling point than cyclohexane in order to obtain paraffin and/or naphthene mixes and/or individual paraffin hydrocarbons (N-hexane) and/or naphthene hydrocarbons (methylcyclopentane, cyclohexane) of commercial purity.

\* \* \* \* \*